(12) United States Patent
Saltsov

(10) Patent No.: US 9,524,377 B2
(45) Date of Patent: *Dec. 20, 2016

(54) MEDICATION DISPENSING AND CONTROL UNIT

(71) Applicant: Leon Saltsov, Thornhill (CA)

(72) Inventor: Leon Saltsov, Thornhill (CA)

( * ) Notice: Subject to any disclaimer, the term of this patent is extended or adjusted under 35 U.S.C. 154(b) by 56 days.

This patent is subject to a terminal disclaimer.

(21) Appl. No.: 14/494,727

(22) Filed: Sep. 24, 2014

(65) Prior Publication Data

US 2015/0012131 A1 Jan. 8, 2015

Related U.S. Application Data

(63) Continuation of application No. 13/442,282, filed on Apr. 9, 2012, now Pat. No. 8,874,260.

(51) Int. Cl.
*A61J 7/00* (2006.01)
*G06F 19/00* (2011.01)

(52) U.S. Cl.
CPC .......... *G06F 19/3462* (2013.01); *A61J 7/0076* (2013.01); *A61J 7/0084* (2013.01); *A61J 7/0454* (2015.05); *A61J 2200/30* (2013.01); *A61J 2205/60* (2013.01)

(58) Field of Classification Search
CPC .......... A61J 7/0084; A61J 7/02; A61J 7/0481; A61J 1/03; G07F 17/0092

USPC .......................................... 700/236, 240, 244
See application file for complete search history.

(56) References Cited

U.S. PATENT DOCUMENTS

| | | | | |
|---|---|---|---|---|
| 5,048,828 A * | 9/1991 | Love | ................ | A63B 69/0002 473/430 |
| 5,152,422 A * | 10/1992 | Springer | ............... | A61J 7/0084 221/2 |
| 5,642,731 A * | 7/1997 | Kehr | .................... | A61J 7/0481 600/300 |
| 7,048,141 B2 * | 5/2006 | Abdulhay | ............... | G07F 11/10 221/3 |
| 8,636,172 B2 * | 1/2014 | Dunn | ........................ | A61J 1/03 221/151 |
| 8,874,260 B2 * | 10/2014 | Saltsov | ................. | A61J 7/0076 700/236 |

* cited by examiner

*Primary Examiner* — Timothy Waggoner

(57) ABSTRACT

A medication and dispensing system tracks the medication of multiple users over time and preferably combines this information with periodic test results provided to the system. The system is designed to allow remote access electronically to authorized users whereby doctors or other medical professionals can review the data of actual medication dispensed and preliminary test results accumulated over time. Preliminary analysis of the data is conducted by the system to identify a predetermined medical alert condition. Upon determination of the predetermined medical alert condition, the dispensing system dispenses or makes available for dispensing an alert response medication.

9 Claims, 37 Drawing Sheets

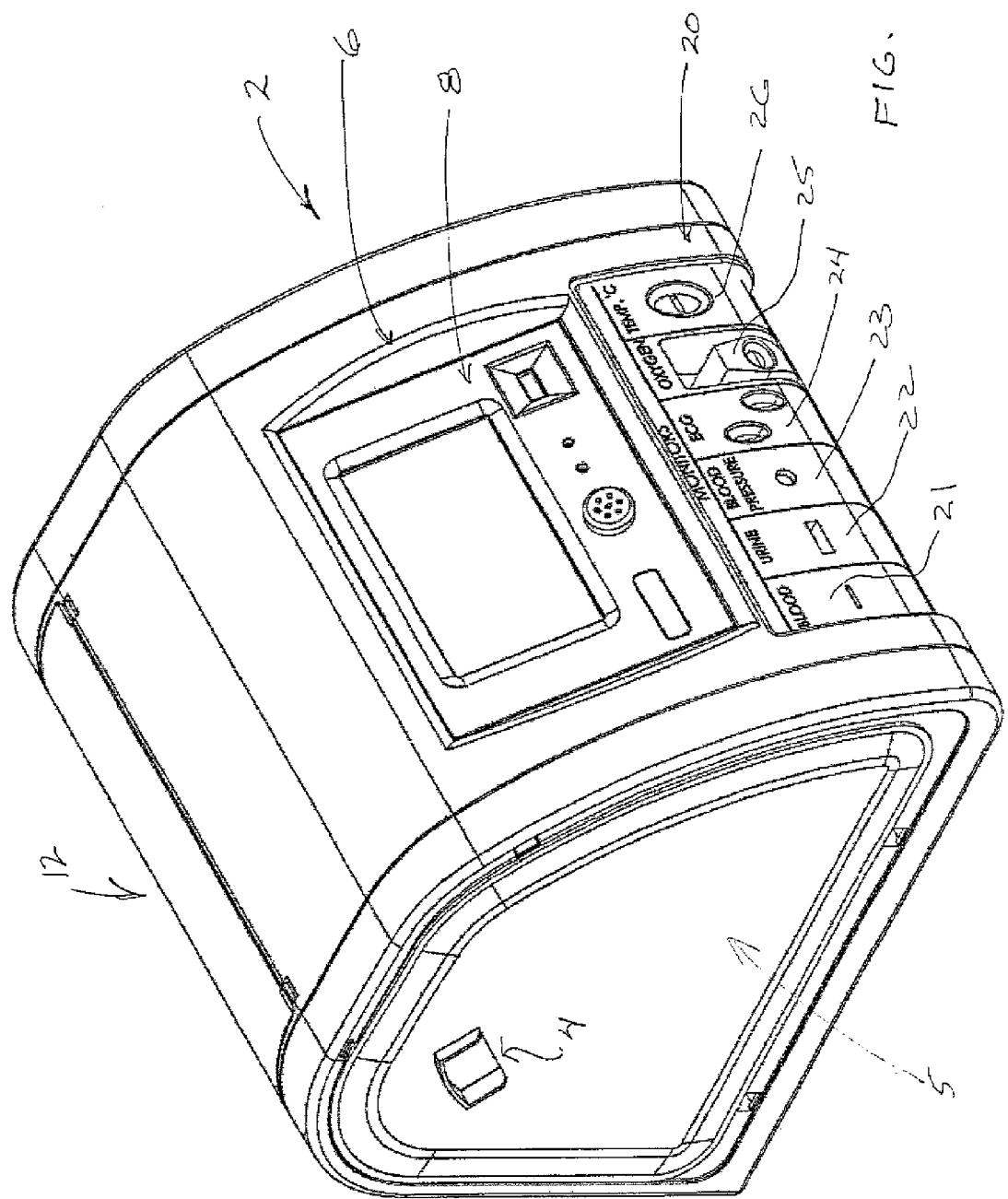

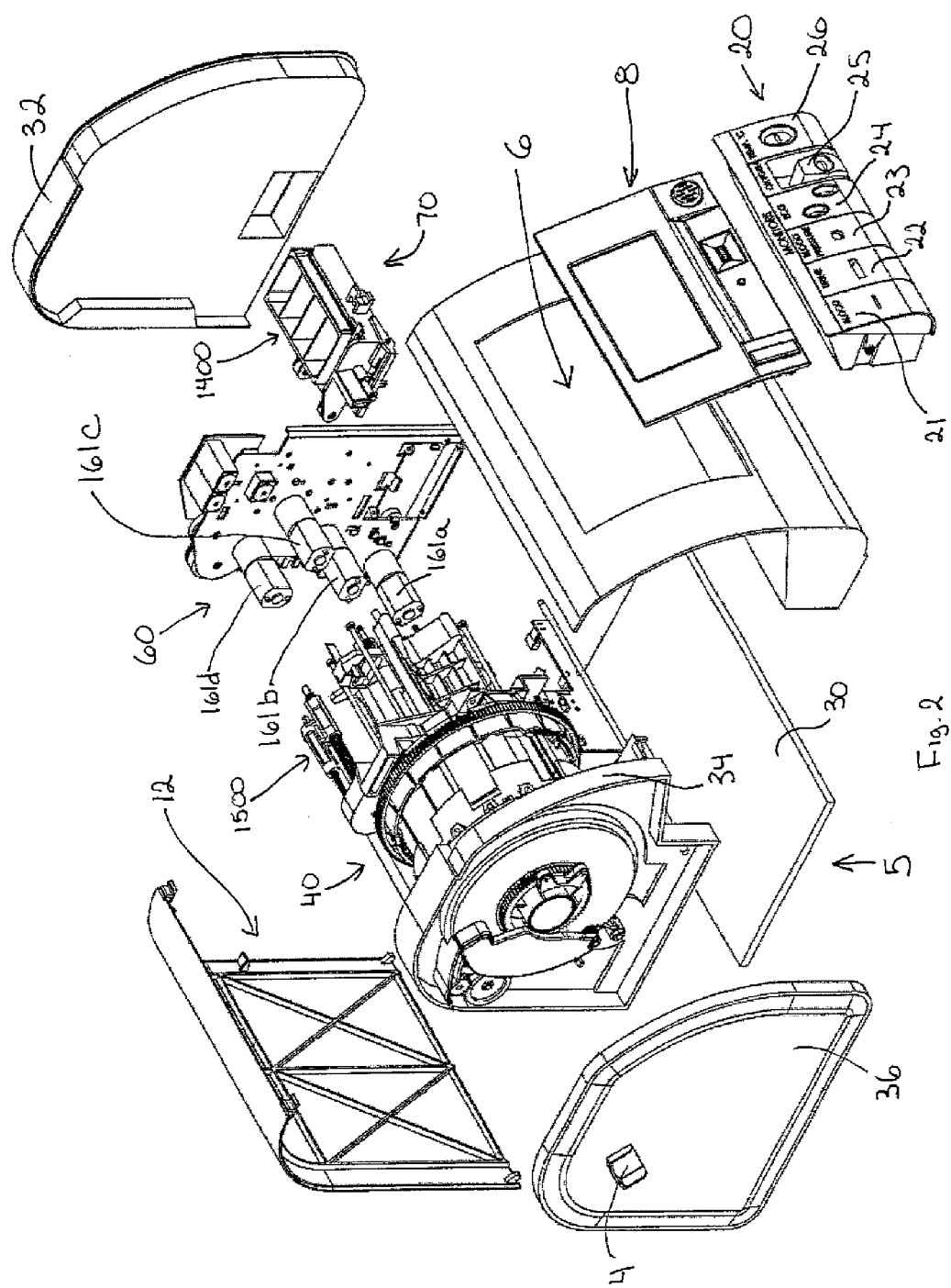

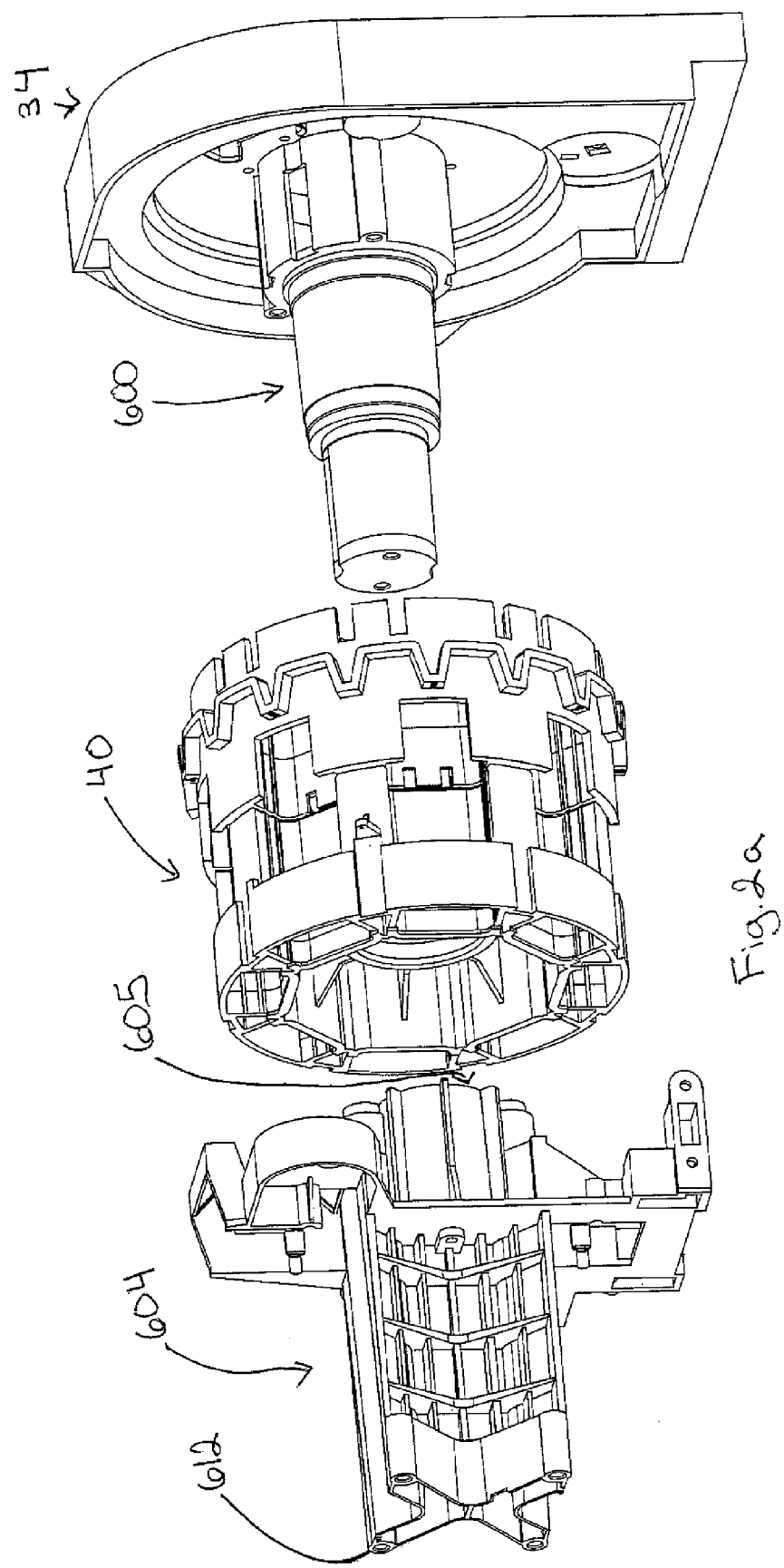

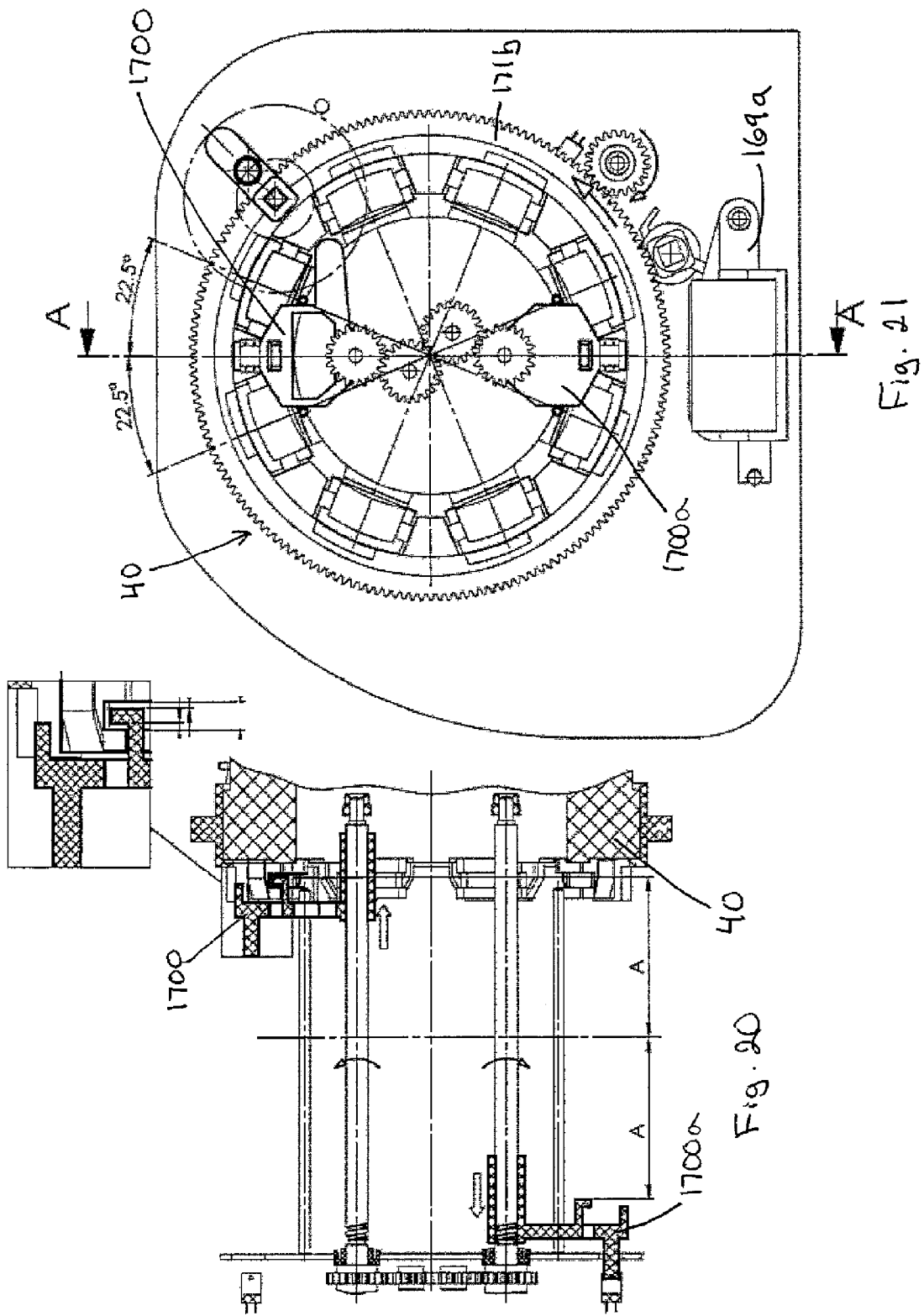

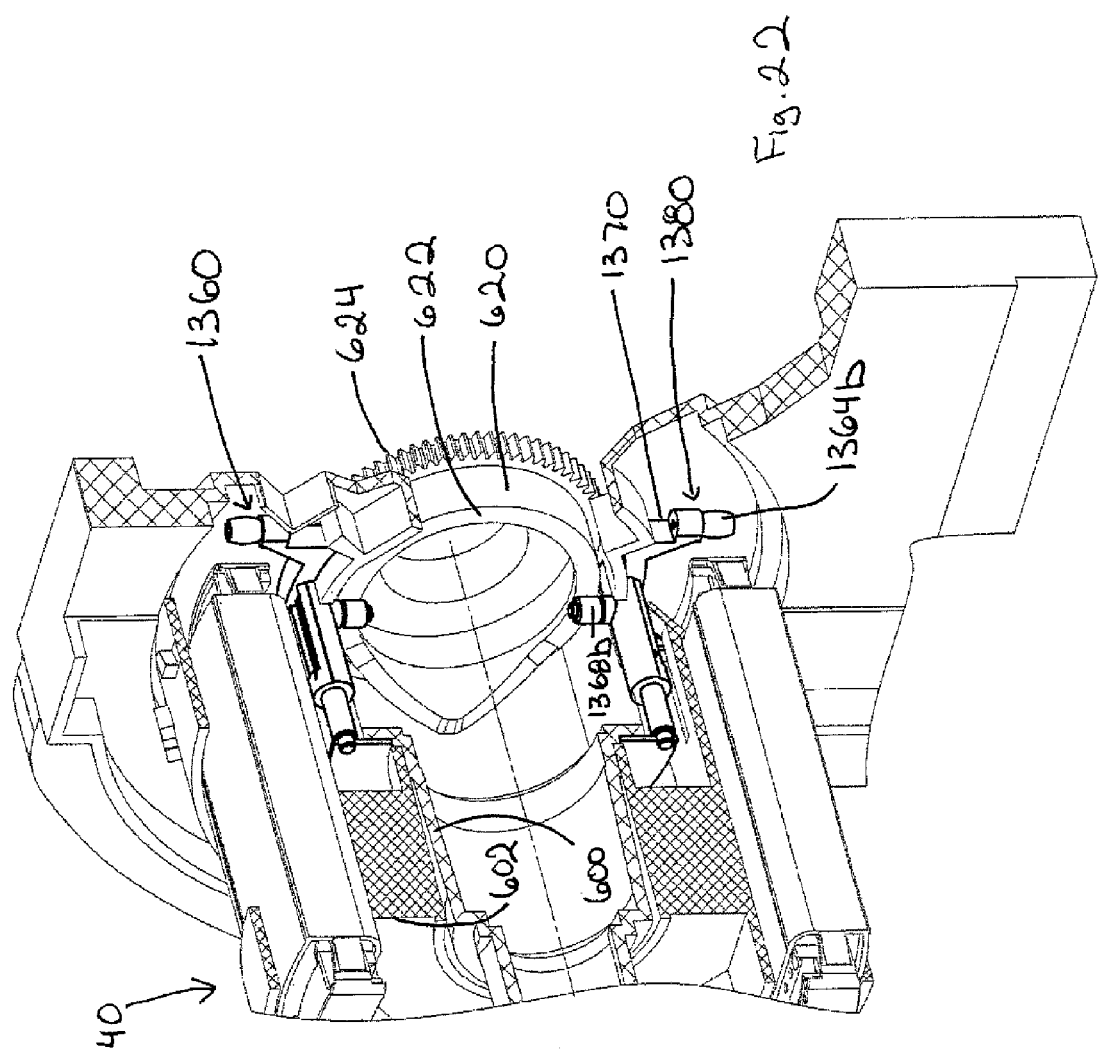

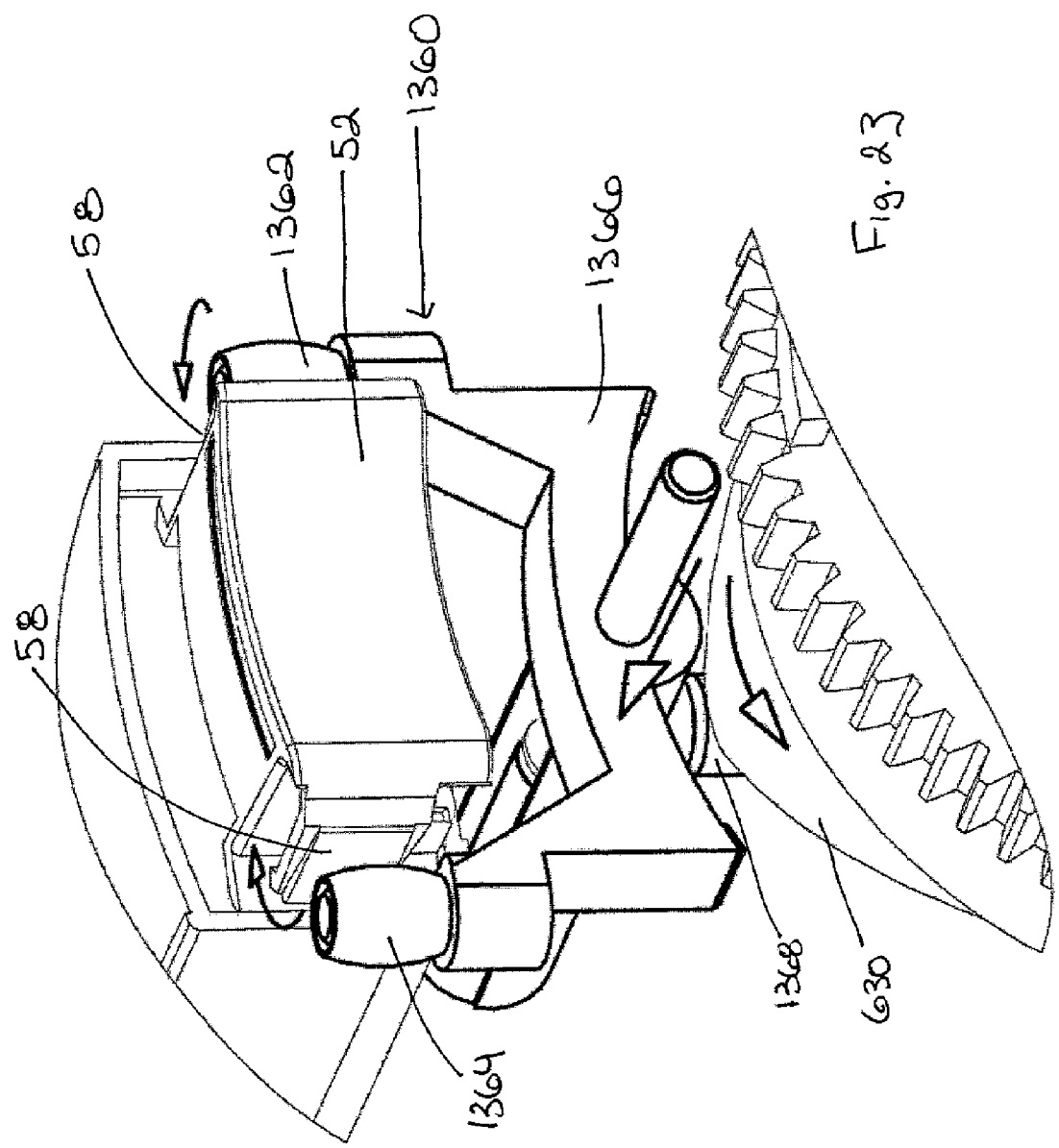

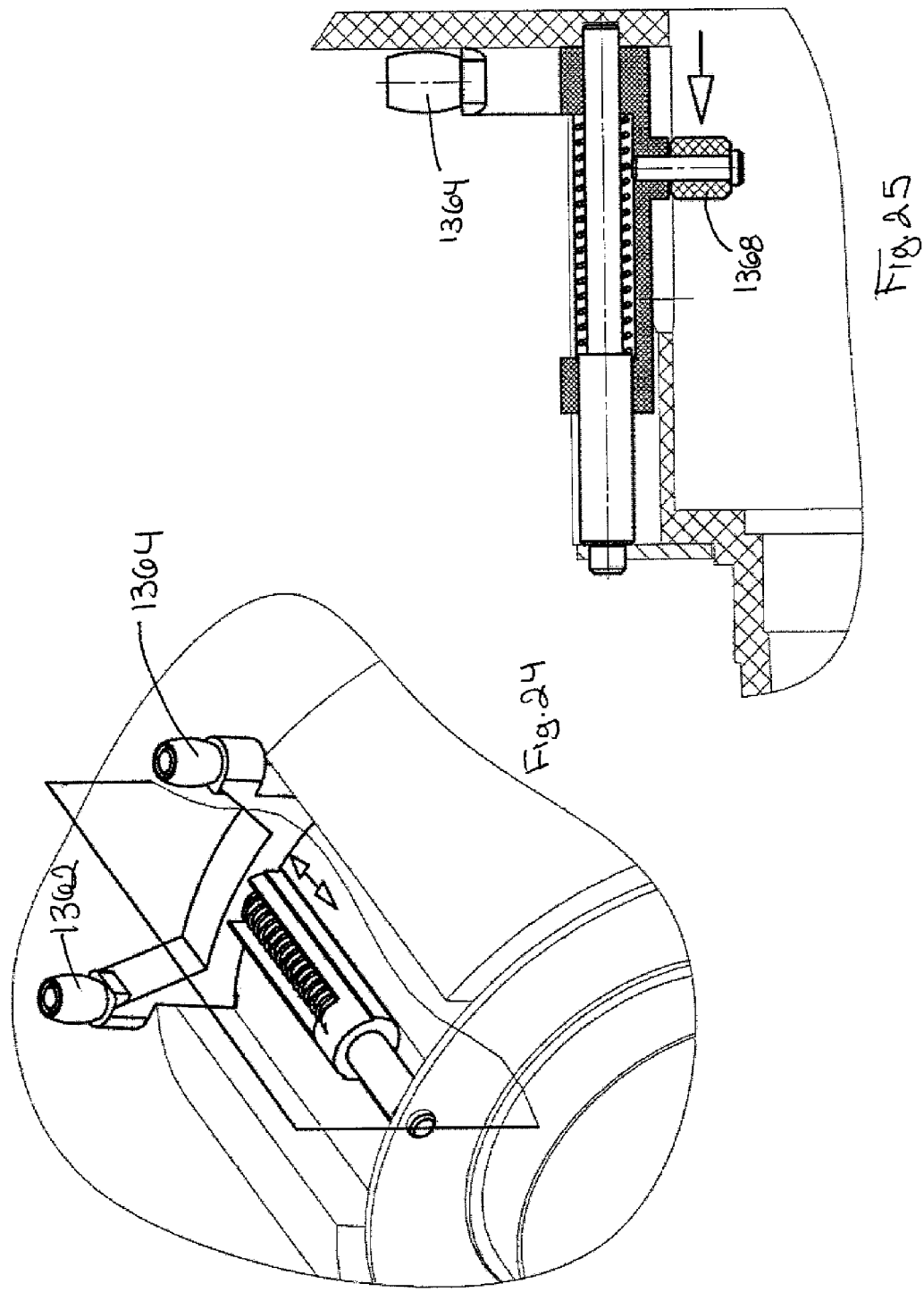

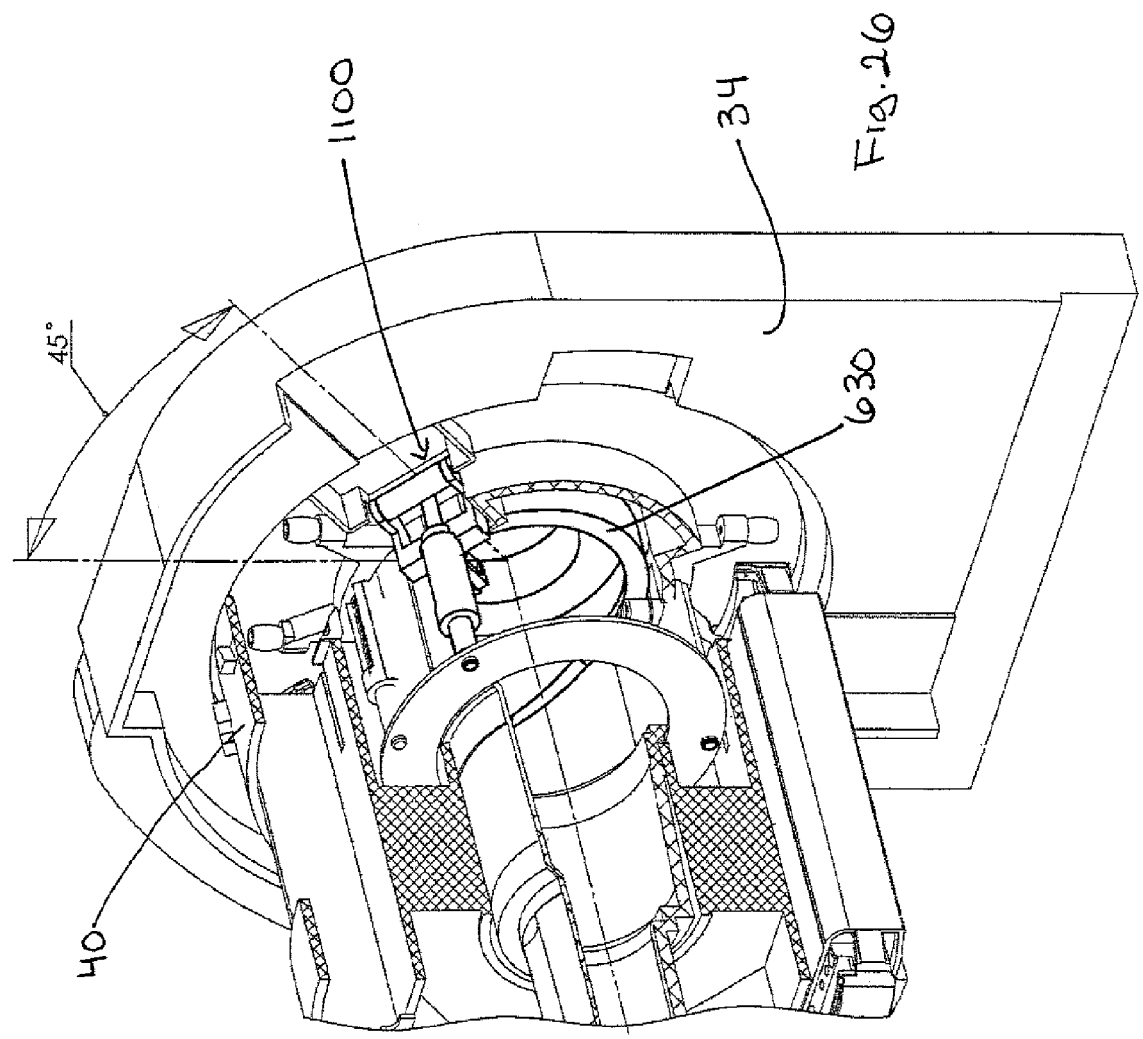

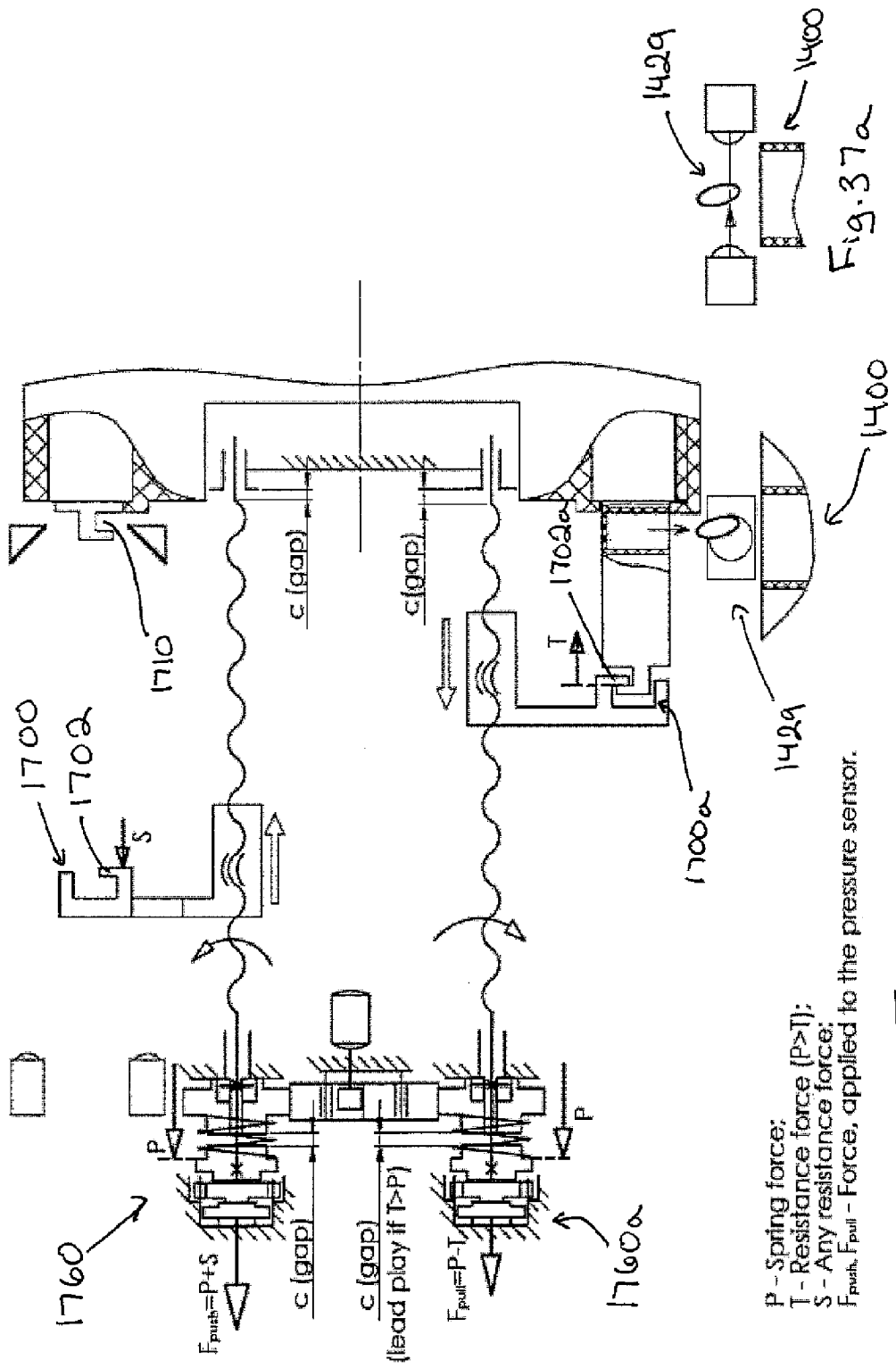

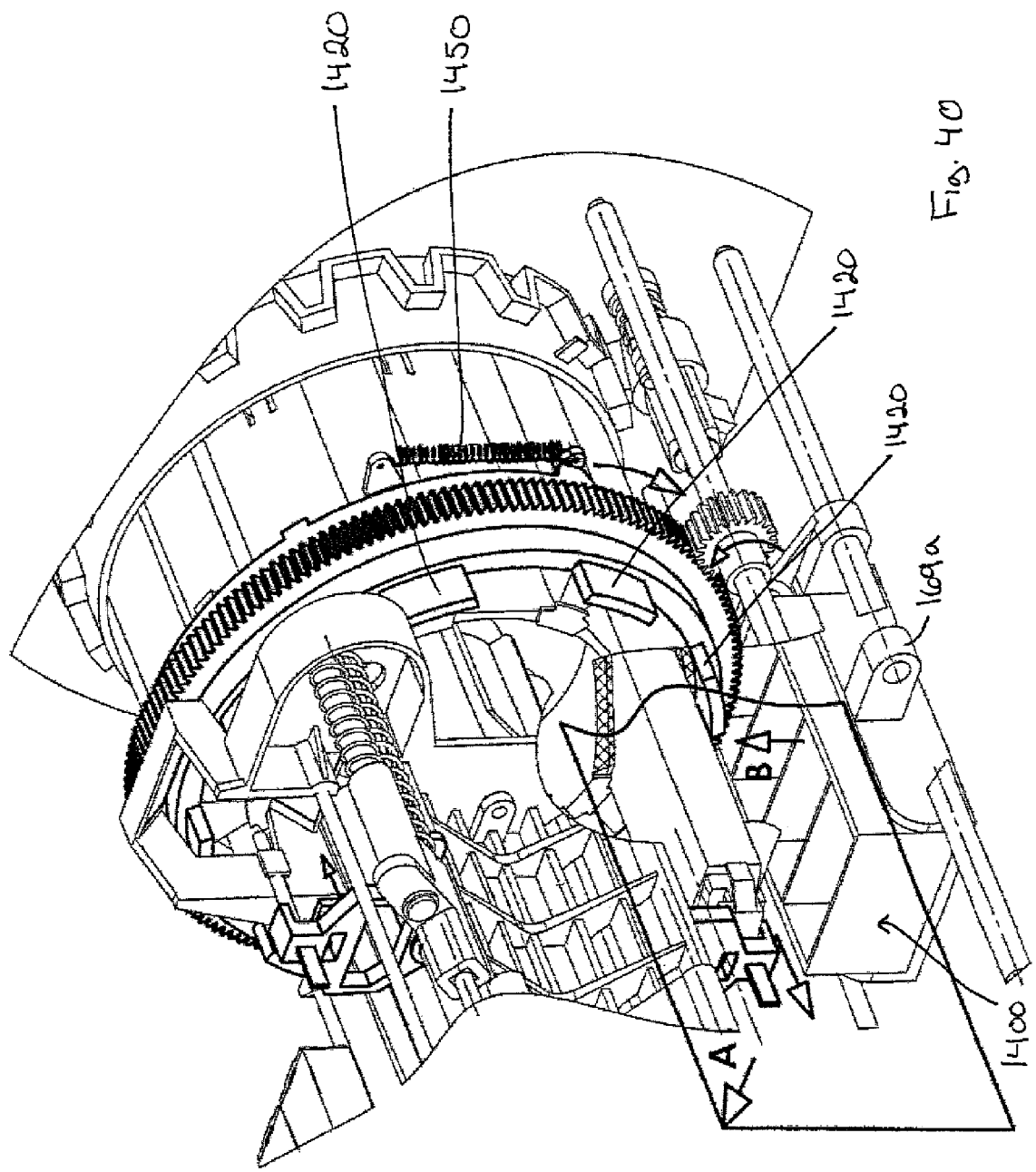

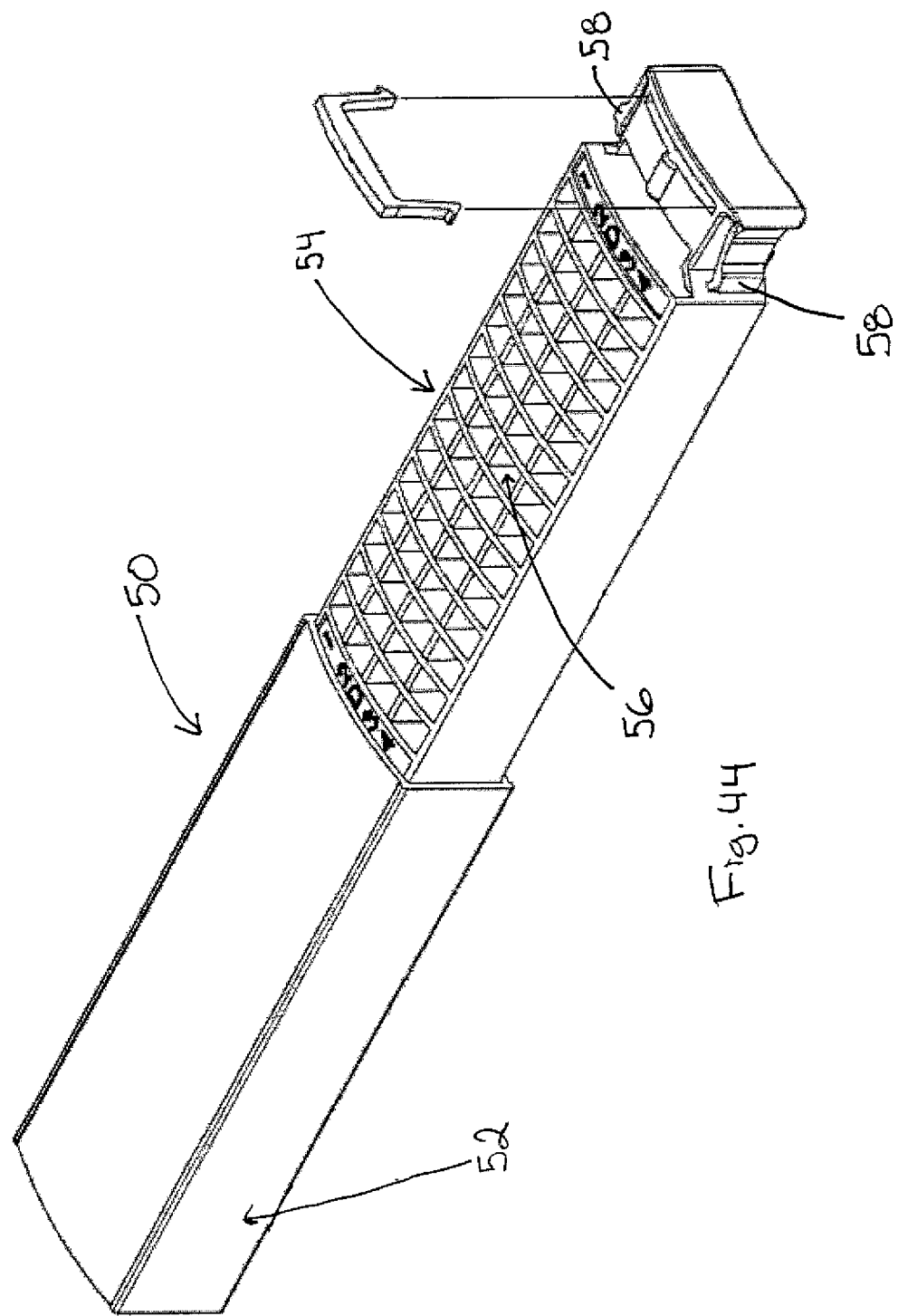

MEDICATION DISPENSING AND CONTROL UNIT

This application is a continuation of U.S. application Ser. No. 13/442,282 filed Apr. 9, 2012 which is a continuation-in-part of International Application No. PCT/CA2011/000457, filed Apr. 26, 2011.

FIELD OF THE INVENTION

The present invention relates to medication and dispensing systems, and in particular to a medication and dispensing system that also provides tracking of the medication over time in combination with periodic user conducted preliminary test results. Analysis of the medication regime and test results can be automatically conducted and optionally remotely managed.

BACKGROUND OF THE INVENTION

A number of different medication dispensing systems have been proposed for home use to assist users in properly dispensing prescribed medication at different times throughout the day and weeks. These systems have not proven entirely effective and often require considerable time to prepare and load medications into the device for proper dispensing. In addition the systems have not recognized or been able to produce a commercial unit that provides for additional control and analysis in the home and preferably allows for remote access.

A medication dispensing system and control unit according to the present invention simplifies the loading of such a system and also allows appropriate loading of a smaller medication organizer for the users daily requirements.

SUMMARY OF THE INVENTION

A medication dispensing and control system according to the present invention receives and controls medication cassettes and to dispense medication retained in a molded core of each cassette. The device includes a computer controller for controlling operation of the device and to maintain an electronic record of medication loaded and dispensed. A rotary drum for receiving medication cassettes is provided at a load position of the rotary drum and the drum is movable to a dispensing position for sequential unloading of cells of any of said medication cassettes. A dispensing container is provided at a dispensing position for receiving dispensed medication suitable for a predetermined period. The computer controller includes an input arrangement for receiving information associated with each received cassette and receiving information regarding medication to be dispensed for the predetermined period. The computer controller controls the device to dispense medication for the predetermined period at the dispensing position and into the dispensing container. The device cooperates to receive test information of any of the users and analysis of the test information for predetermining alert conditions. Upon detection of an alert condition an alert response medication stored in the device is available for dispensing.

BRIEF DESCRIPTION OF THE DRAWINGS

Preferred embodiments of the invention are shown in the drawings, wherein:

FIG. 1 is a perspective view of the medication dispensing and control unit;

FIG. 2 is an exploded perspective view of the medication dispensing and control unit;

FIG. 2a is an exploded perspective view showing the support of the rotatable drum of the unit;

FIG. 20 is a view similar to FIG. 19 showing additional details of the upper and lower extractors;

FIG. 21 is a left end view of FIG. 20;

FIG. 22 is a partial perspective view showing details of the upper and lower sliders and a rotatable drive cam;

FIGS. 23 and 24 show additional details of the upper slider arrangement;

FIG. 25 is a sectional view along line A-A of FIG. 24;

FIG. 26 shows further details of the rotatable cam, the rotatable drum and a cassette lock arrangement;

FIG. 37 is a schematic showing the positioning of the extractors during dispensing of medication;

FIG. 37a shows details of a light sensor for detecting medication as it is being dispensed;

FIG. 40 is a partial perspective view showing the rotatable drum and the rotation of baffles associated with the rotatable drum for dispensing of medication and generally are similar to View B of FIG. 38;

FIG. 44 is a perspective view of the medication cassette where the cartridge of the cassette is partially withdrawn from the sleeve.

DETAILED DESCRIPTION OF THE PREFERRED EMBODIMENTS

Figure 3:
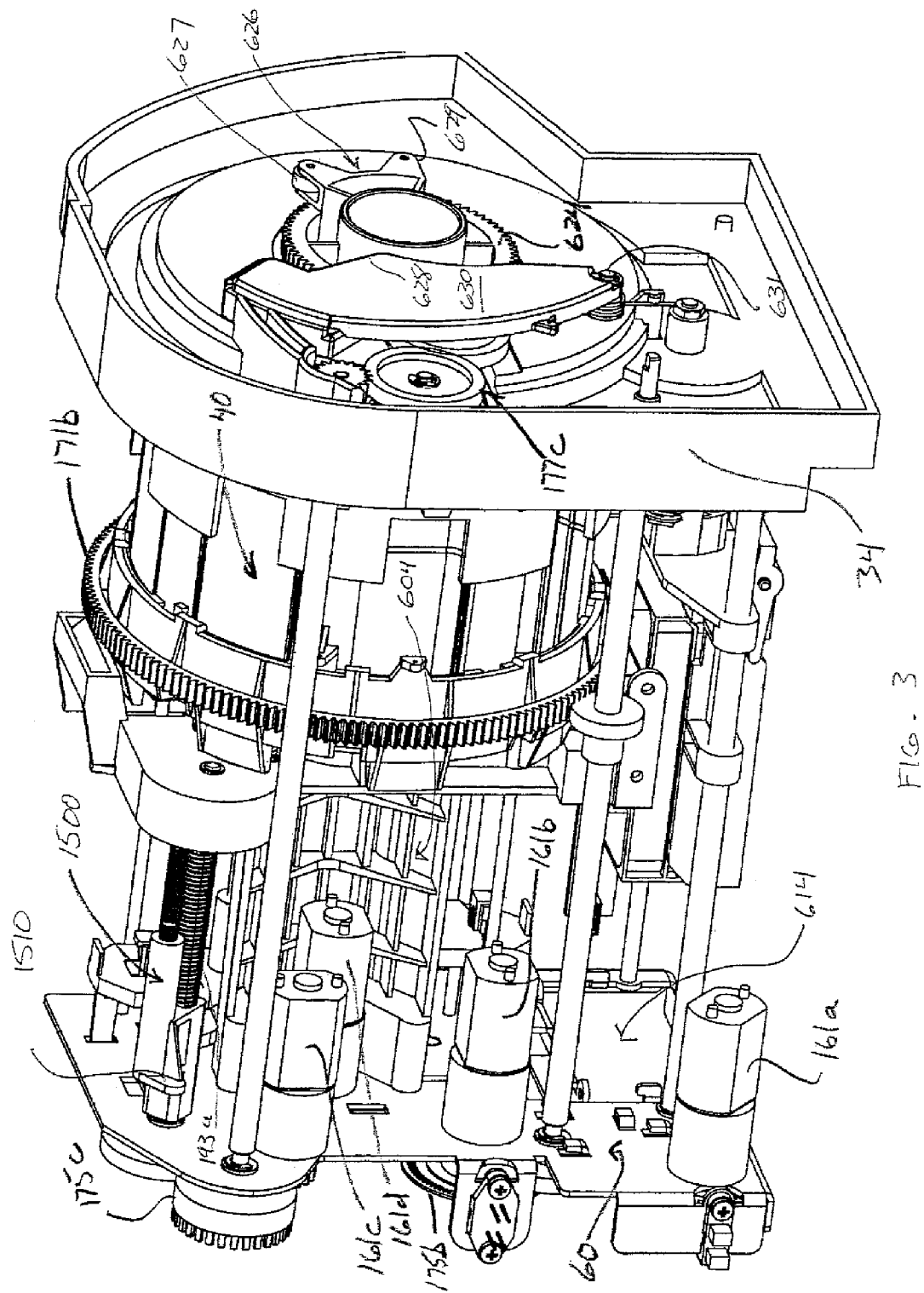
FIG. 3 is a perspective view of the working components of the medication dispensing and control unit.

The medication dispensing and health assessing system 2 shown in FIG. 1 is provided to assist one or more users in dispensing of medication, tracking of medication and providing a preliminary assessment with respect to the user's ongoing health. The health assessment provision can be added at a later point in time if not provided with the original unit. For many patients tracking and assisting in daily medication needs may be sufficient. In other circumstances the capability to track test results relative to medication dispensed, can be of great assistance in investigating for example sudden changes in health.

As shown in FIG. 1, the system 2 includes a medication cassette input port 4 in one end of a housing 5, and as will be subsequently described, a series of prepackaged medication cassettes are received in the rotatable drum 40 (FIG. 2) for controlled dispensing of medication. A user interface 6, in this case a touchscreen input module, is provided on a front face of the system to allow a user to input critical information and to interact with and instruct the system. A series of input/output connections 8 are provided below the user interface 6. These connections 8 allow the system to connect with other devices for inputting information (including test results) and/or outputting information including communication signals (including signals containing collected information for medical review).

The test input module 20 includes a connection for blood analysis 21, a connection for urine analysis 22, a connection for blood pressure assessment 23, an ECG test 24, an oxygen test 25 as well as temperature assessment 26. Typically these connections provide inputs for each of these tests and other connectable devices perform these functions. The results of these tests are received and retained in the system 2 and are available in combination with the particular medication dispensing regimes that occur over time and are tracked by the user. This allows improved time analysis of medications and any side effects or changes in conditions and a preliminary assessment of the user's health. These and other test functions are tracked by the system.

One of the advantages of the present system is the ability to perform a number of relatively simple tests at different points in time and to maintain the results of such tests. For example, a user may take certain medications at different times throughout the day and it may be desirable to conduct these tests at least once a day or perhaps at a time associated with each dispensing of medication. This combined information associated with the actual medication that has been dispensed, as well as the test results conducted over time, provide an accurate record of information not normally available. This information remains stored in the system and can be communicated to a doctor or other medical service provider if required. The system 2 can carry out a preliminary computer analysis to provide daily or ongoing alerts and provide feedback through the user interface to the user or to a remote contact person. As can be appreciated dispensing of medication and optionally tracking of test results occur to provide a history of information that may be helpful as part of an ongoing or selective medical assessment.

Pre-authorized contacts can electronically receive this information (for example, through internet/telephone transmissions). Also the user can receive communications from remote medical professionals by a suitable electronic communication to the device or directly to the user. These communications can be alerts or an alert message that further investigation is needed.

The system 2 monitors for compliance/non-compliance of the medication regime of different users and includes a remote communication of these results. For example, for an elderly patient living independently, a family member could be authorized to receive automatic reports regarding daily medication or to receive an alert in the event of non-compliance. Similarly, test results can be provided. In this way tracking of medication and actual results can be used to provide early identification of problems or changes in health. In addition the system can act as a reminder for medication that is not stored such as eyedrops etc. Also scheduled tests and/or appointments can be tracked and communicated to the system and tracked.

The system also allows for the manual entry of symptoms, aches and pains, or side effects to provide additional documented information. The system is also capable of wireless communication with alert bracelets etc. for emergency contact. For example, if a person fell a transmitter/receiver carried by the person could be actuated to provide emergency assistance through the telecommunication capabilities of the system 2.

Testing may be carried out by the user when a side effect or change is being experienced to provide better information for subsequent analysis. At the present time, these results are only tracked if a user has experienced a problem and a medical professional is investigating. Typically the user is in a health facility to provide these results. The present system avoids or reduces or supplements this procedure for many patients.

The medication dispensing and health assessing system 2 is designed to assist a user with respect to daily dispensing of medication and also, in combination with other existing equipment, to perform simple monitoring tests and recording of information as generally described above. The system provides preliminary analysis. Authorized medical personnel can access the device remotely as may be required from time to time or as part of an assessment of a current or recent change.

A further advantage of the system is to allow a synergistic function of the dispensing and testing functions. For example in case of high blood pressure medication and testing, a variable dispensing of medication can be prescribed by a doctor to address a possible outcome recognized by the doctor and programmed in the system. For example in the event of detected high blood pressure exceeding a certain point, the system may temporarily dispense an additional medication to address this problem and communicate the same to the doctor. In this example the doctor knew of the possibility of excessive high blood pressure and basically prescribed for a normal and an excessive condition to be determined by testing. As can be appreciated this principle can be used in other circumstances to tailor medication to meet the conditions determined by testing monitored by the system.

Figure 43:
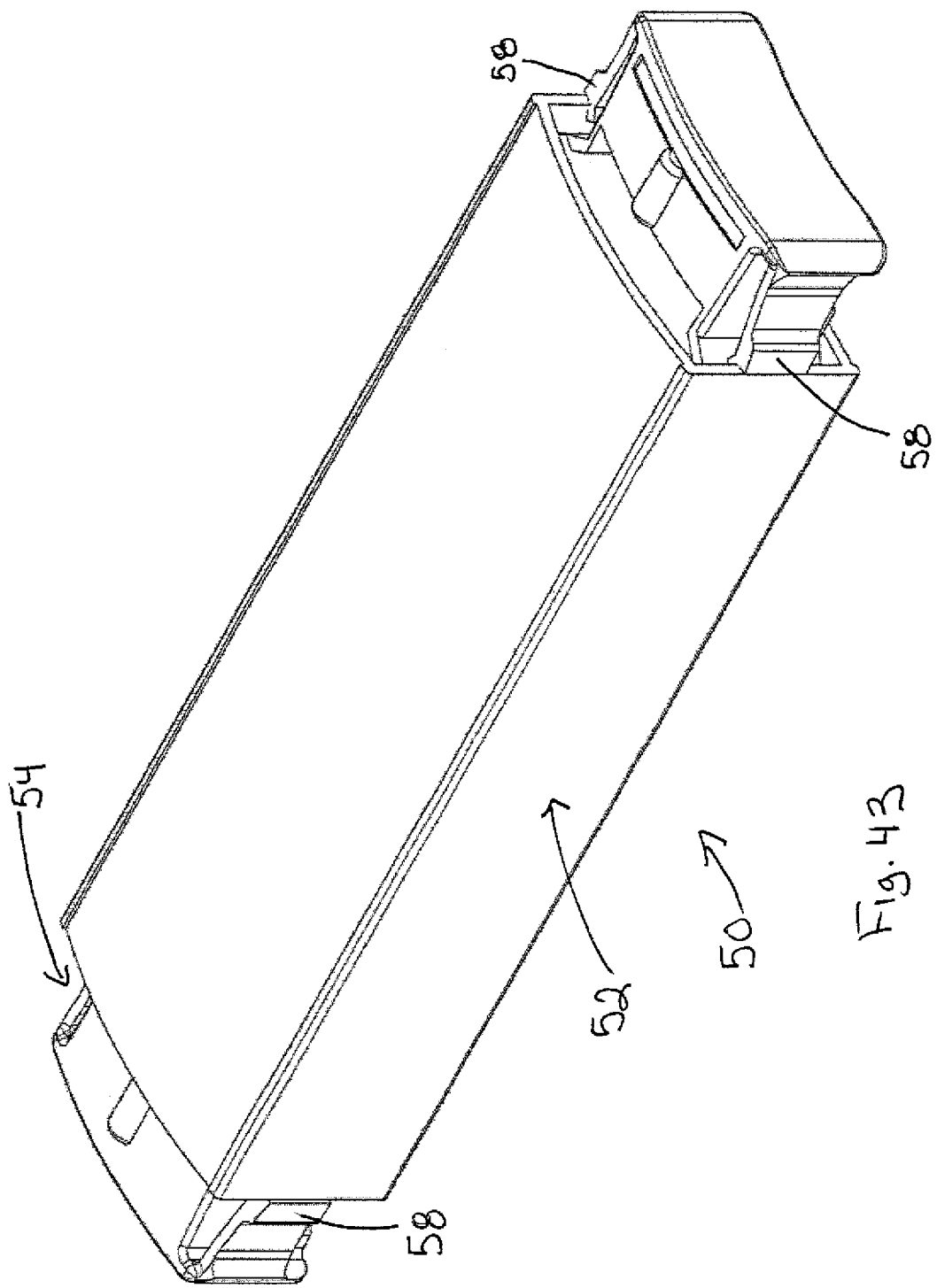
FIG. 43 is a perspective view of the preferred medication cassette.

The preferred medication cassette is disclosed in co-pending Canadian application 2,646,029 filed Dec. 9, 2008 incorporated herein by reference. The medication cassette 50 includes an outer sleeve 52 in combination with a sliding core 54. The sliding core 54 has a series of cells 56. For convenience the medication cassette is shown in FIGS. 43 and 44. Preferably the medication cassette includes a RFID tag identifying information regarding the user, the medication and dosage etc that is read or determined by the medication and dispensing system when inserted in the system.

The medication cassette 50 preferably is preloaded for a particular patient and can be inserted through the cassette input port 4 shown in FIGS. 1 and 2. Full details of the medication cassette, per se, are not required to understand the operation of the medication dispensing and health assessing system 2. It is sufficient to say that the medication cassette can be preloaded with a particular medication and the cassette can have different configurations of cells provided in the sliding core or cartridge 54 that slides within the sleeve 52. The medication dispensing and health assessing system 2 receives this cassette and appropriately process it, as will be subsequently described. The cassette preferably includes machine recognized information including identification of the medication, the patient and the dosage regime. This information can be provided in a number of different manners including labeling, querying, electronic tagging, downloading of information, etc. The cartridge 54 also includes spring arms 58 at either end of the sliding core 54 that are moved inwardly to allow one set of the spring arms and the ending of the sliding core 54 to enter the outer sleeve 52 to allow dispensing of medication at the opposite end of the sleeve.

FIG. 2 is an exploded perspective view of the medication dispensing system 2 and illustrates the assembly of the overall system and the components and functions of the device. As shown in FIG. 2, the device includes a support base 30 with a support end member 34 and a cover 32 at opposite ends of the housing. Support end member 34 also includes an end cover 36. A rotatable drum 40 forms one of the critical components of the system and this drum is rotatably supported on a support shaft 600 extending from end member 34 towards the metal support member 60.

Rotatable drum 40 is basically supported on a stationary interior support shaft 600 in combination with component support member 604 shown in FIG. 2*a*. The component support member includes a center port 605 that is secured to the end of support shaft 600. The rotatable drum includes its own interior bearing 602 rotatably supporting the drum on support shaft 600. As shown in the cutaway drawing of FIG. 22 the interior bearing 602 supports rotatable drum 40 on the support shaft 600 and capture the drum between end member 34 and component support member 604 (see FIG. 2*a*). Basically component support member 604 receives the end surface 606 of the support shaft 600 and serves to maintain the rotary drum on the rotary shaft with very little end to end play. The drum gear 610 effectively controls the position of the drum on the support shaft 600 and is used to appropriately position the drum. End 612 of the component support member 604 is supported at its free end by the metal support member 60 shown in FIG. 2.

As shown in FIG. 22 the end support member 34 also supports the rotatable cam 620 having the cam surface 622. The cam drive gear 624 (see FIG. 3*a* and FIG. 22) controls the position of the rotatable cam 620 and it also controls the position of the bifurcated actuating arm 626. In FIG. 22 the end support member 34 is shown partially cut away. The bifurcated actuating arm 626 (FIG. 3) includes two rollers (627, 629) at the free ends of the arm which contact the cam surface 628 of the pivoting shutter 630. The shutter 630 is spring biased to close the access port 4*a* in the end support member 34. The shutter 630 also closes the port 4 in the cover 36. In the position shown in FIG. 3*a* the shutter 630 closes the passageway between ports 4 and 4*a* and maintains these ports closed until the bifurcating arm 626 causes the shutter 630 to pivot about shaft 631 opening ports 4 and 4*a* such that a medication cassette can pass through ports 4 and 4*a* into a slot of the drum. This opening of the ports is timed to the position of the bifurcated arm 626 with the cam surface 628. The rotatable cam 620 is driven by a reversible motor and the shutter 630 remains closed unless a cassette is to be loaded or ejected from the rotatable drum.

With the arrangement as described, the end support member 34 supports the support shaft 600 and the end of the support shaft is also supported by the metal support 60 through the component support member 604. The rotary drum at one end of the system 2 accommodates receipt of medication cassettes and the space to the opposite side of the rotary drum is used to access the cartridges 54 of the cassettes at the 12 o'clock and 6 o'clock positions for checking and dispensing of medication respectively.

The rotary drum 40 preferably includes eight slots 700 (see FIG. 6) distributed about the periphery of the drum. As can be appreciated less slots are possible for a lower capacity system and the system can work well with 3, 4, 5, 6 or 7 slots. Each slot receives a medication cassette therein and provides a significant capacity of medication to be dispensed. Basically the sleeve of the cassette is fully received in the rotary drum and the locking spring arm members 58 of the cartridge extend either side of the drum. Initial insertion of a cassette into a slot causes inward camming of the first spring arms due to the shape thereof. Once the cassette is properly received the spring arms are accessible for release of the cartridge. One set of the spring arms adjacent the support member 34 must be forced inwardly to allow the cartridge of the cassette to slide partially through the drum either for counting of the medication in the cells or for sequential dispensing of medication stored in the cells of the cassette as will be later described.

As can be appreciated from a review of FIGS. 1 and 2, the input port 4 is at a 45 degree angle of advance relative to top dead center of the drum. Thus the medication cassettes are loaded through the ports 4 and 4a when a slot 700 is aligned with the ports and the shutter 630 is moved to the clear position. Basically the user pushes the cassette into port 4 and into a slot 700 of the rotary drum. There is a spring bias applied against the cassette to provide some resistance and the medication cassette is moved outwardly if it is not fully received in the drum. When the medication cassette is properly received in the drum it is effectively locked in the drum and the drum can then be moved to one of the two working positions (12 o'clock or 6 o'clock) in addition to the cartridge receipt position.

The 12 o'clock position is used to allow counting of the medication within the cells of the cassette. The cassette includes machine readable information regarding the patient for whom the medication is destined as well as the details regarding the storage of the medication within the individual cells of the cassette. These cassettes include different cell configurations to accommodate different sizes of medication and therefore the device is provided with information regarding the cassette configuration. The device progressively withdraws the cartridge from the sleeve at the 12 o'clock position to scan and confirm that a pill is in each cell of the cassette if it has been filled. Once the medication has been counted and confirmed, the cartridge is returned into the drum and is fully received within its own sleeve and will rotate with the drum.

The 6 o'clock position of the drum is used to allow dispensing of medication within a particular cassette. Basically the cartridge is partially withdrawn at the 6 o'clock position and the drum is controlled such that each cell of the medication cassette in each row of the cassette is progressively exposed. In this way the individual cells are sequentially uncovered and any medication within the particular cell is dispensed by gravity into a receiving receptacle. This receiving receptacle is designed to receive the medication in a container suitable for the end user. For example, the medication may be for a particular day or time period. It is common to load a patient's daily dosage of medication in individual cells labeled for the appropriate times.

In order to accomplish these functions the system includes top and bottom extractors at the 12 and 6 o'clock positions to effectively allow withdrawal of a cartridge from the sleeve and reinsertion thereof. The top extractor sequentially exposes each row of cells at the 12 o'clock position and a light scan confirms that medication is received in each cell as specified in the electronic information. At the 6 o'clock position sequential dispensing of medication in each cell of a row occurs. As can be appreciated the top and bottom extractors effectively withdraw the cartridge of a cassette from the drum to allow the appropriate steps to be carried out and these extractors also allow the cartridge to be reinserted into the drum. The extractors have a common drive but only one extractor is working at any point in time. The device also includes a biasing and a release arrangement to allow a dispensed medication cartridge to be aligned with the output ports 4 and 4a and ejected from the drum under the assistance of an ejector.

Figure 27:
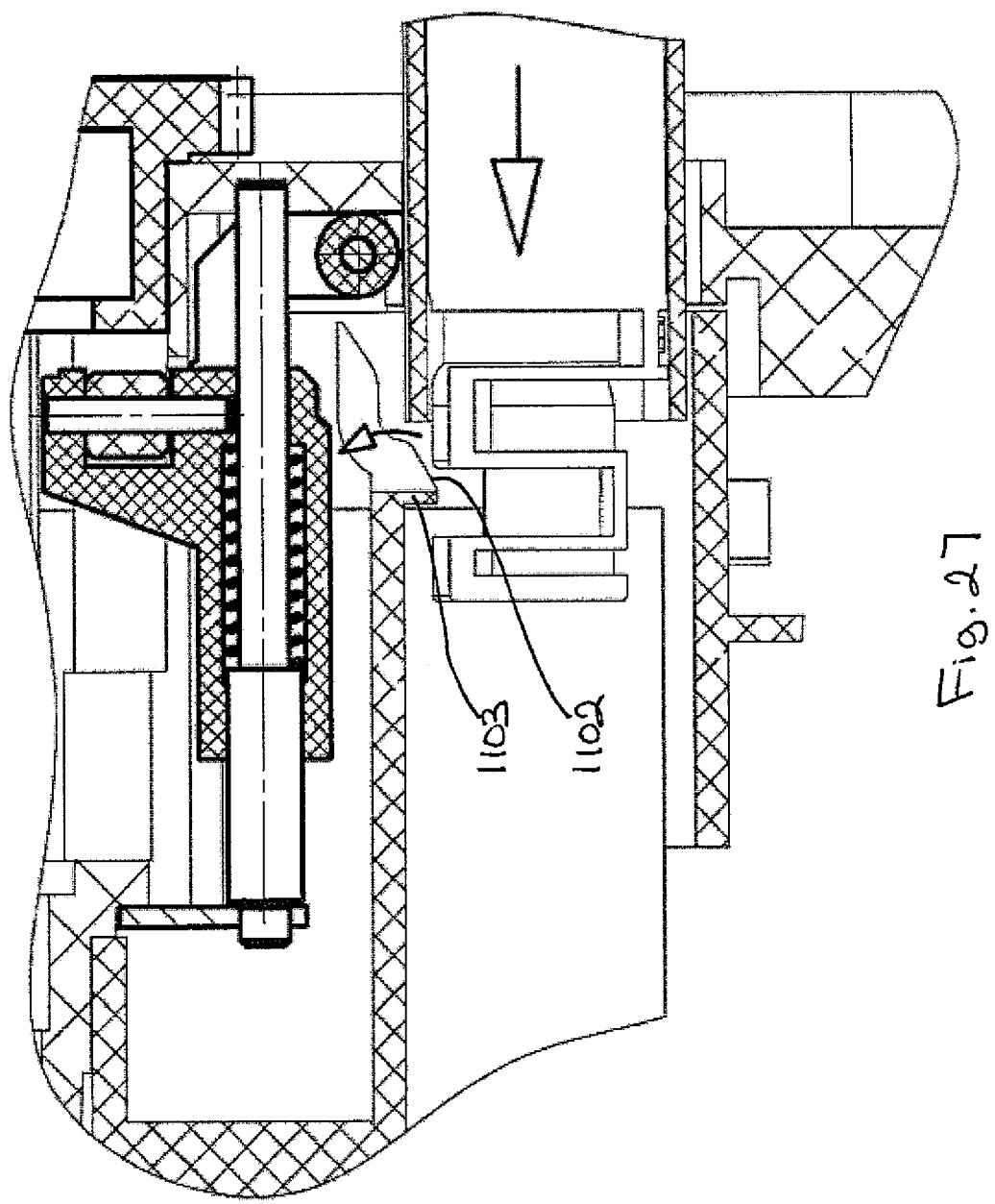
FIG. 27 is a partial side view showing insertion of a cassette into a receiving slot of the rotatable drum.
Figure 28:
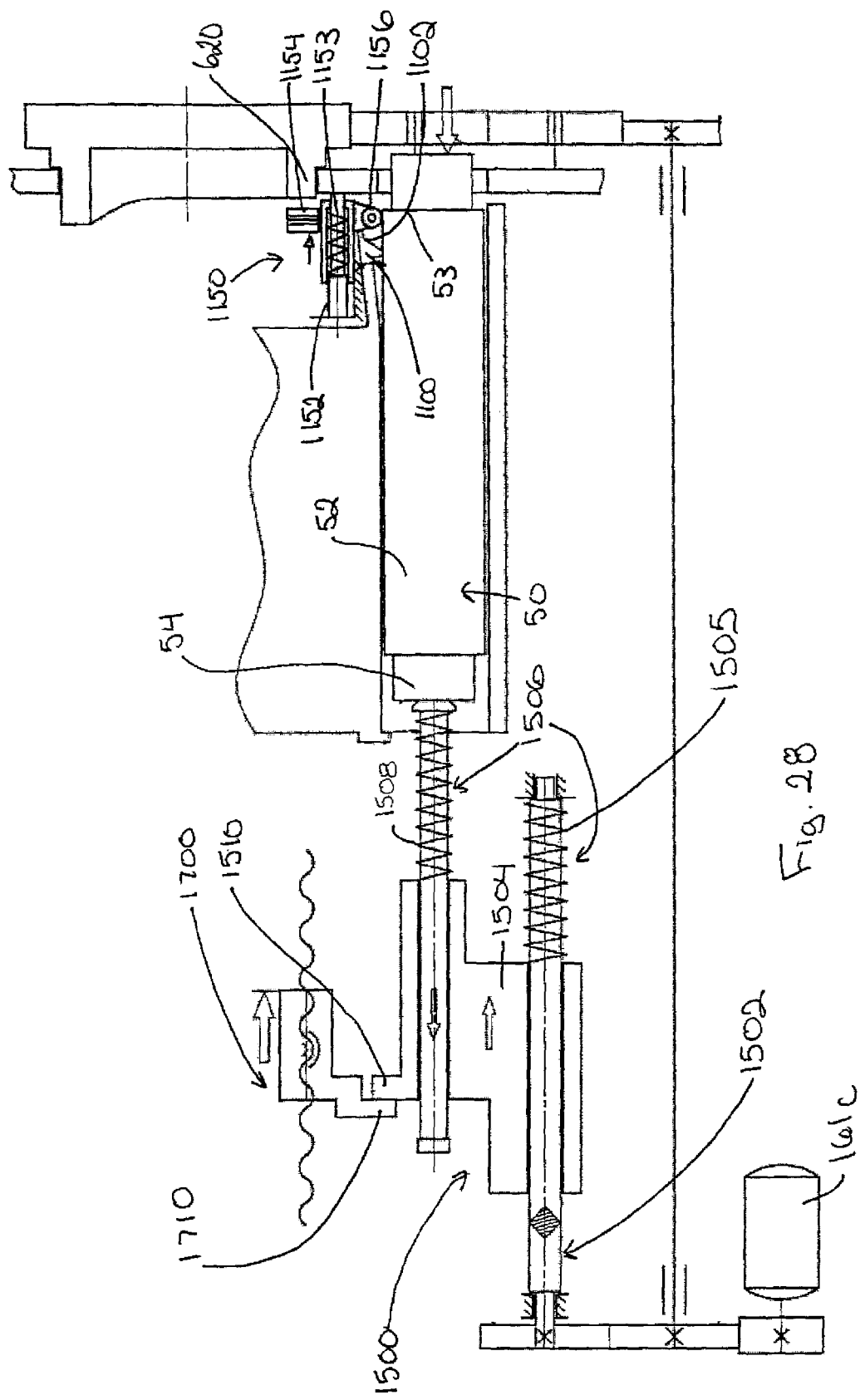
FIG. 28 shows additional details of a cassette being inserted into the rotatable drum and having a bias applied thereto by an ejector plunger.

With the present system, the medication cassettes are inserted by hand through the port 4 and into an appropriate slot 700 of the rotating drum 40. As part of the insertion of the cassette it is important to accurately locate the medication cassette within the drum. In the present system the cassette is inserted against a spring force where a plunger type member is biased against a spring as the cassette is being manually pushed into the appropriate slot within the rotatable drum. A spring latch 1100 of the rotary drum 40 (FIGS. 27 and 28) operates to appropriately lock the sleeve of the medication cassette and also the cartridge of the cassette in a predetermined loaded position within the drum. FIGS. 27 and 28 show the medication cassette being inserted into a slot 700. The rotatable cam 620 is partially shown in the figures and is used to control a number of components including the spring latch 1100 during ejection of a loaded cassette from the rotatable drum.

Each of the slots for receiving a medication cassette includes the spring latch 1100. This spring latch includes a cam face 1102 that engages the end of the cassette and cams upwardly as the cassette is pushed into the appropriate slot. This allows the latch edge 1103 to move to a raised position. As shown in FIG. 28 the latch edge 1103 will snap inwardly engaging the end 53 of the sleeve 52 once the cartridge is properly received in the drum 40. This allows the latch edge 1103 to move to a raised position. The spring latch 1100, when latch edge 1103 has moved inwardly, acts as a stop for the end 53 of the sleeve 52. A spring bias is exerted by the rotatable ejector arrangement 1500. The ejector arrangement 1500 exerts a force on the cartridge 54 of the medication cassette 50 and as this cartridge is effectively stopped against the spring latch 1100, the cartridge is accurately positioned in the rotatable drum.

Figure 30:
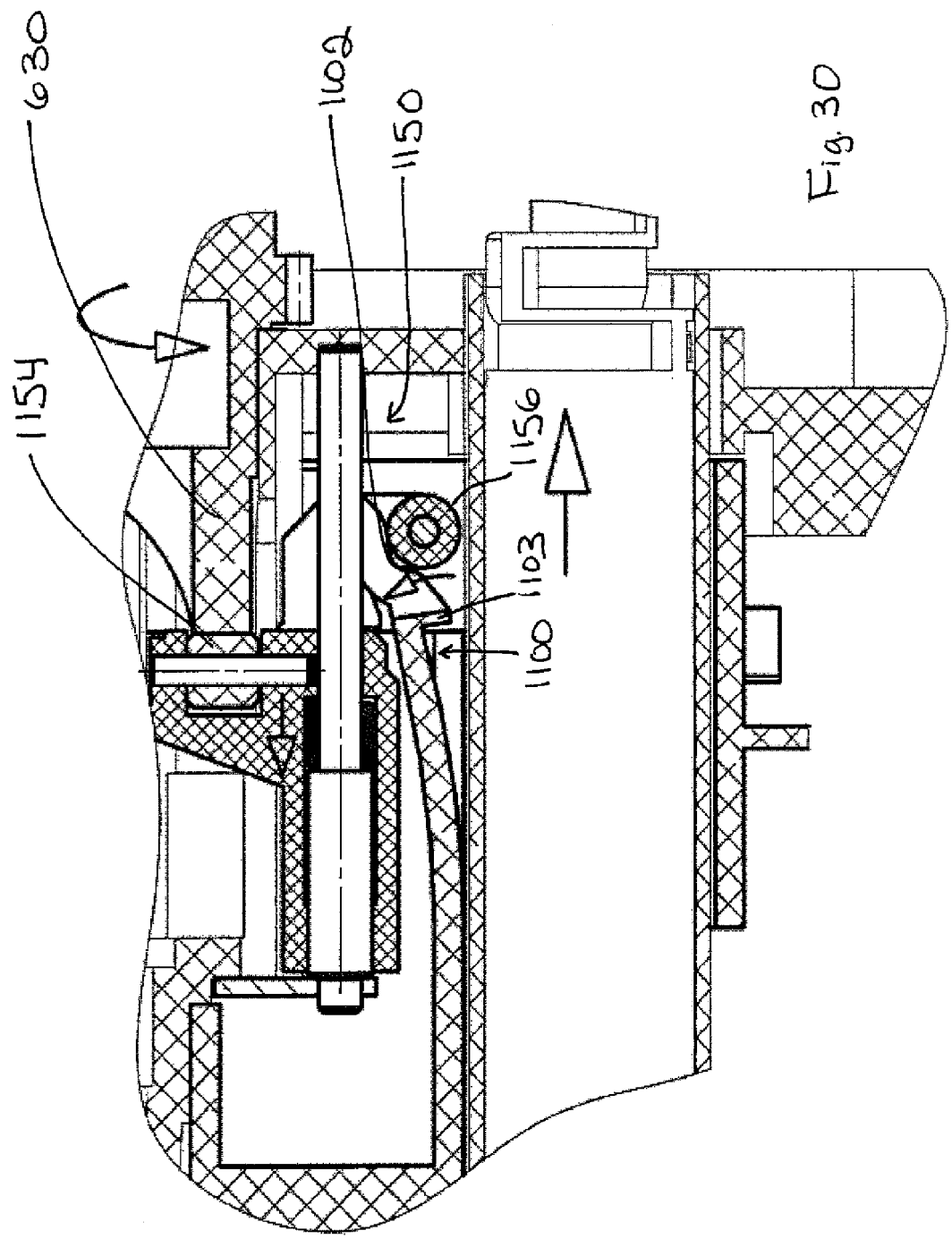
FIG. 30 shows additional details of the release of the medication cassette from the rotatable drum.

To release a cartridge, a spring latch actuator shown as 1150 slides on rod 1152 and is biased by spring 1153 such that the roller 1154 is urged against the rotatable cam 620 (see FIG. 30). The actuator 1150 when forced to the left by the rotatable cam 620 causes the roller 1156 to engage the spring latch 1100 and move the latch upwardly. This upward movement of the spring latch 1100 releases the cartridge that is biased by the spring force of the ejector arrangement 1500 and moves partially out of the receiving slot of the drum. As will be further described, the ejector plunger is then driven towards the right to further eject the medication cassette from the drum. This ejection of the medication cassette is carried out once the medication in a cassette has been fully dispensed or an instruction signal has been received to remove the particular medication cassette.

FIG. 30 shows the rotatable cam 620 and the roller 1156 is also visible in the drawing. The spring latch arrangement 1100 is associated with each slot and each slot cooperates with the latch actuator 1150 when it is in the 45 degree position in advance of top dead center. FIG. 30 shows the position of the spring latch 1100 during ejection of the cassette and as can be seen the roller 1156 has now engaged surface 1102 of the spring latch and has biased the spring latch upwardly to allow ejection of the cassette. The rotatable cam 620 is in engagement with the roller 1154 and has caused this particular movement to allow the medication cassette to be manually or automatically removed from the drum.

As can be appreciated from a review of FIGS. 27, 28, 29 and 30, the rotatable cam 620 is rotated to cause a desired movement of a spring latch 1100 used to lock a medication cassette in the rotatable drum once the cassette has been fully inserted therein. A spring bias is continually exerted against the cassette during insertion and the spring latch accurately determines the lengthwise position of the medication cassette in the drum.

Figure 29:
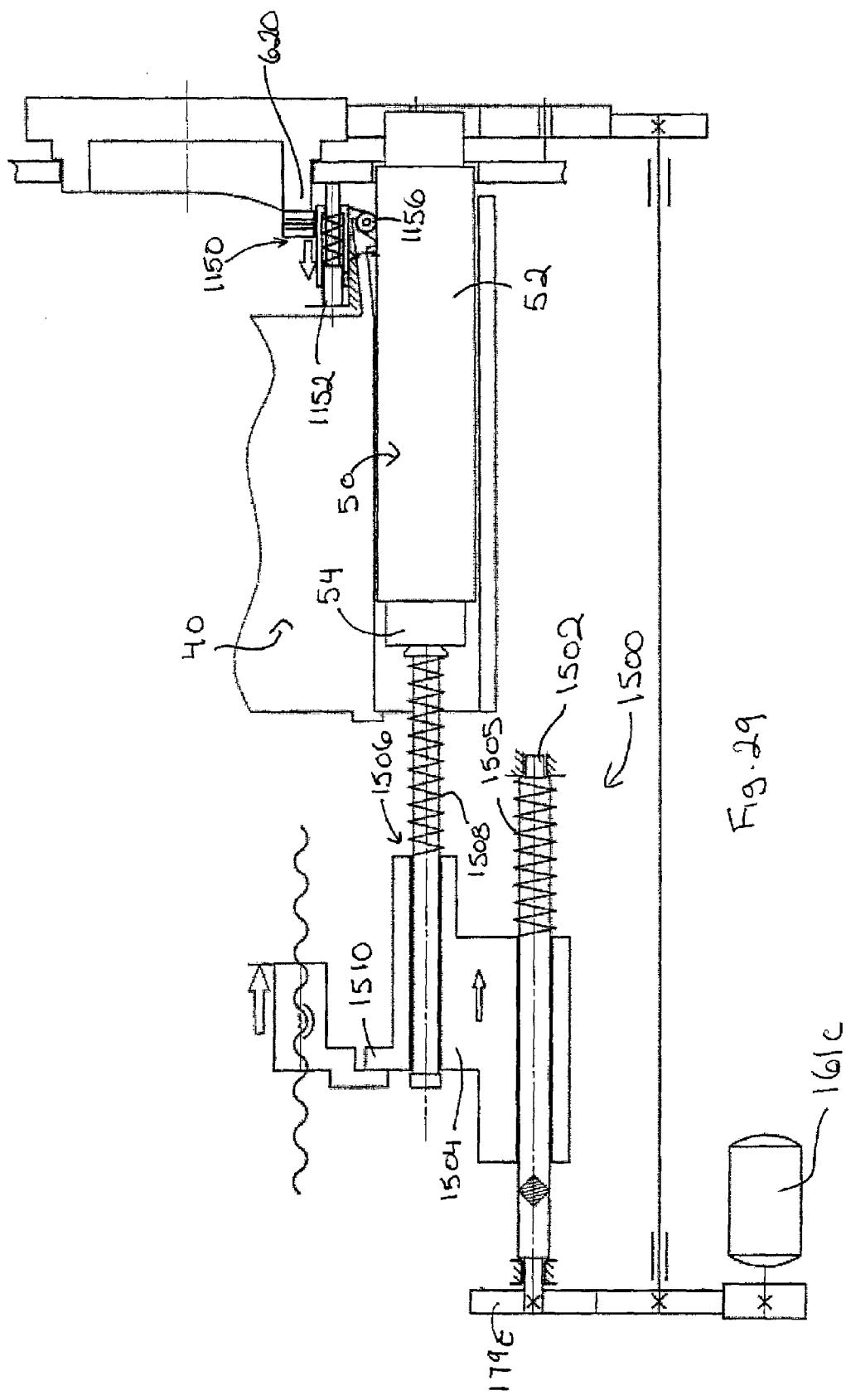
FIG. 29 shows the ejection of a cassette from the rotatable drum.

Other arrangements can be used for accurate positioning of a medication cassette within the drum however this arrangement makes use of the rotatable cam that is also used for the movement of other components including the shutter latch 630 and the sliders. FIGS. 28, 29 and 30 show the relationship of the rotatable cam 620 and the roller 1156 relative to the insertion slot.

Once a medication cassette has been appropriately inserted into the rotatable drum 40, the ejector arrangement 1500 is rotated out of the way to a clear position adjacent the exterior of the drum. The drum is rotated to move the cassette to the 12 o'clock position. At the 12 o'clock position the cartridge of the medication cassette is sequentially withdrawn and scanned to provide an electronic signal of the details of the medication stored therein. This information and details of the particular type of cassette are automatically entered in the computer system of the device. To conduct the scan, the cartridge is progressively withdrawn from the sleeve to extend beyond the opposite end of the rotary drum. The cartridge is sequentially withdrawn to expose each row of cells.

Figure 33:
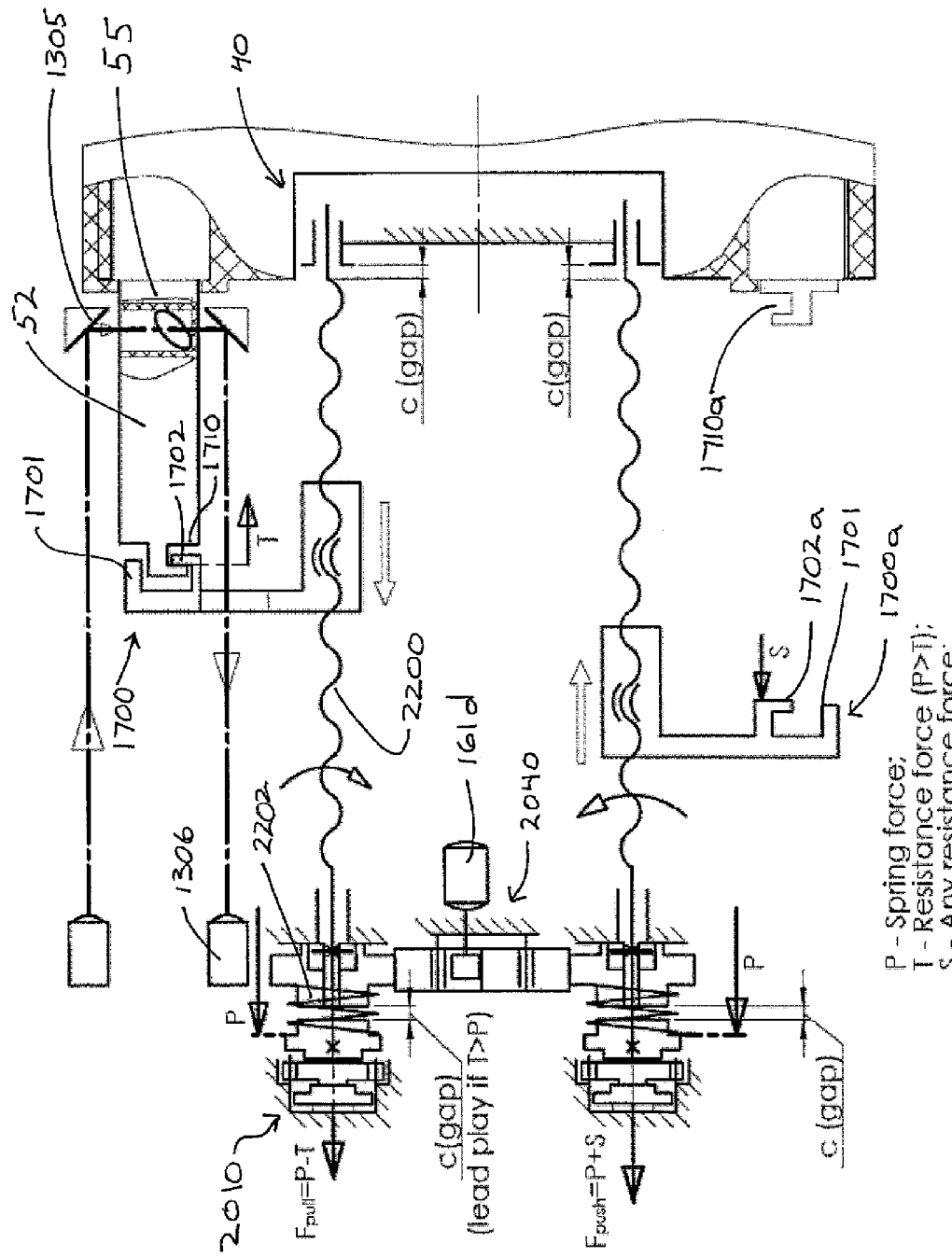
FIG. 33 shows additional details of the counting of pills at a 12 o'clock position of the rotatable drum.
Figure 34:
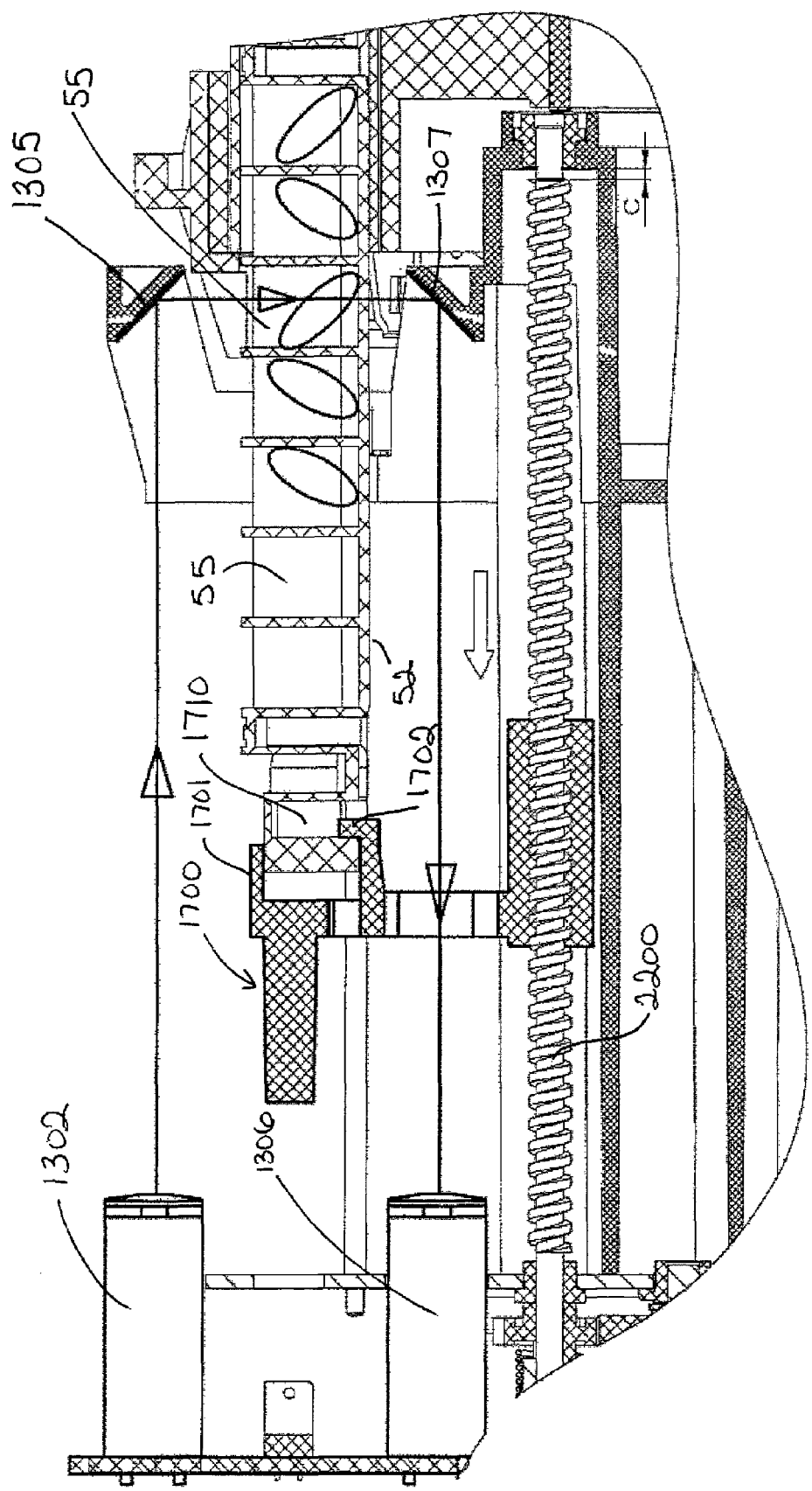
FIG. 34 shows additional details of the counting of pills when a medication cassette is inserted in the device of plane A of FIG. 35.
Figure 35:
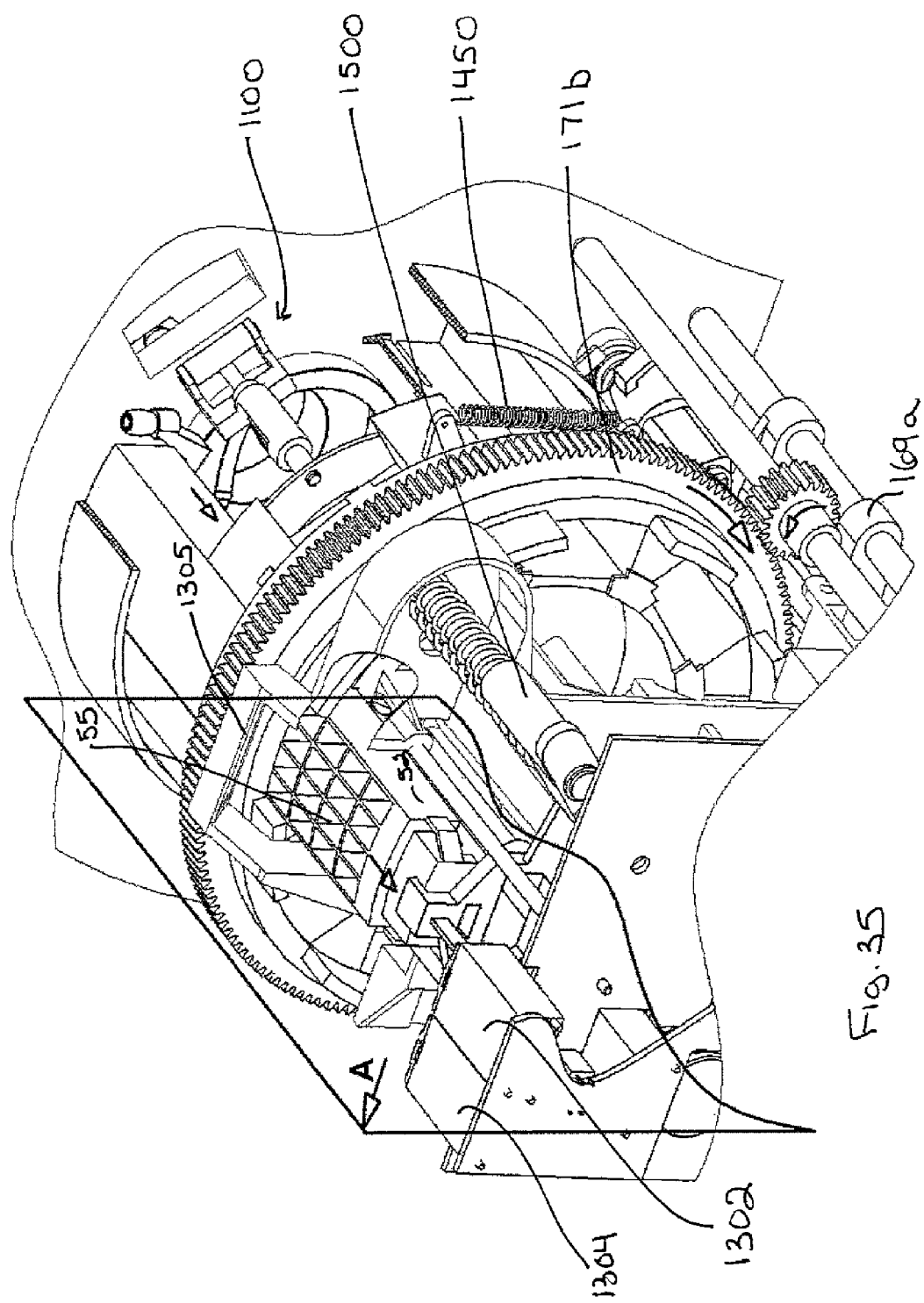
FIG. 35 is a perspective view showing details of the counting of the medication.
Figure 36:
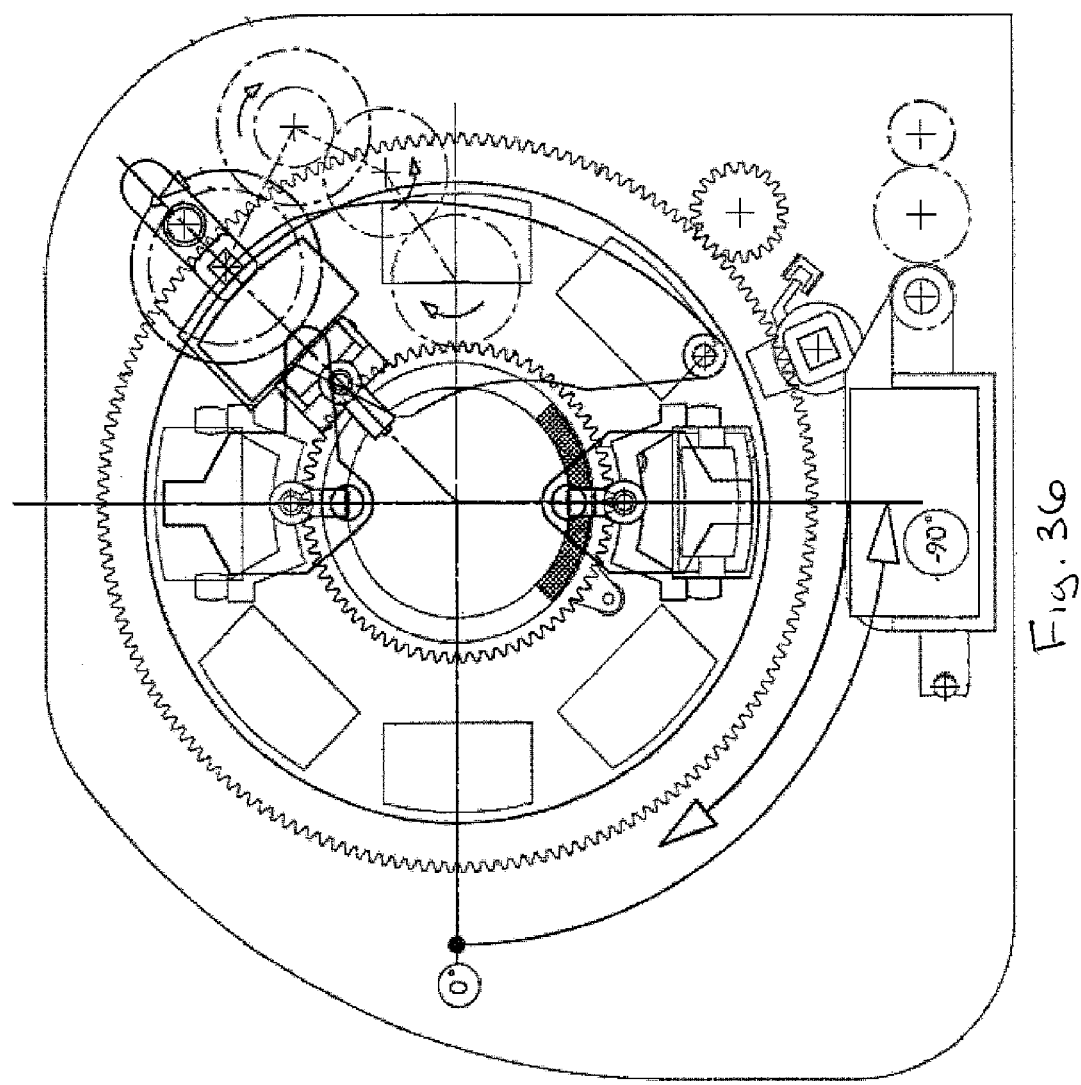
FIG. 36 is an end view showing various components in position for dispensing medication.

FIGS. 33, 34 and 35 show partial removal of the cartridge 52 as it is withdrawn from the rotatable drum 40. The individual cells 55 of the cartridge 54 have a light beam arranged for passing the generally transparent bottom of the cartridge 54 such that light emitted by emitters 1302 and 1304 towards the mirror 1306 is deflected downwardly into each cell. Each of the light emitters includes a light beam used to scan two cells of a four cell row cartridge. A movable baffle of the rotary drum 40 allows sequential exposure of the cells that is later described. It is possible to use four light emitters one for each cell. In the embodiment shown the light emitters are appropriately activated such that each cell can be considered independently. In any event a pill within one of the individual cells being scanned interrupts the light beam and thus interrupts the light which is returned to the light receiver 1306. This light receiver separately evaluates the light signals thereby confirming that a particular pill of medication is positioned within each of the cells. As can be appreciated the light deflected downwardly by mirror 1305 also cooperates with a mirror 1307 on the underside of the cartridge to direct the light rearwardly to the light receiver 1306. Thus there is a light passage above the cartridge and a light passage below each cartridge whereby light transmitted from the light emitters 1302 and 1304 finds its way to the light receiver 1306 unless interrupted by a pill. A top extractor 1700 sequentially removes the cartridge 52 from the rotatable drum 40 until all cells 55 are progressively scanned.

Before the cartridge 54 may be removed or pulled outwardly of the rotatable drum 40 it is necessary to disengage the spring arms 58 of the cartridge adjacent the opposite end of the drum (i.e. at the end of the drum adjacent the input port). This disengagement is shown in FIGS. 22 through 26. The rotatable cam 620 is also used to control a top slide actuator 1360 which is forced by the rotatable cam 620 from right to left towards the drum and parallel to the axis of the drum (see FIG. 23). This causes a pair of rollers 1362 and 1364 to engage the spring arms 58 of the cartridge 52 and forces the spring arms inwardly. As can be seen, rollers 1362 and 1364 are located on the slider 1366 which includes the roller 1368 in engagement with cam 620 to force the slider towards the cartridge and the drum. The slider 1366 is also spring loaded to be biased against the cam surface. In this way, the slide actuator 1360 automatically retracts when it is not necessary to engage the spring arms to allow the cartridge to move out of the drum. A similar lower slider actuator 1370 for movement of cassette spring arms is provided at the 6 o'clock position to again engage the spring arms and allow withdrawal of the cartridge to allow for dispensing.

Additional details of the top and bottom slide actuators are shown in FIGS. 24 and 25. The cam 620 engages the roller 1368 of the upper slider or roller 1368*b* of the lower slider to cause the slide actuator to move and cause rollers 1362 and 1364 of the upper slider or rollers 1362*b* and 1364*b* of the lower slider to engage the spring arms and push them inwardly. A similar release of the spring arms is carried out at the 6 o'clock position and is controlled by the cam 620 and the lower slider actuator 1380.

Figure 42:
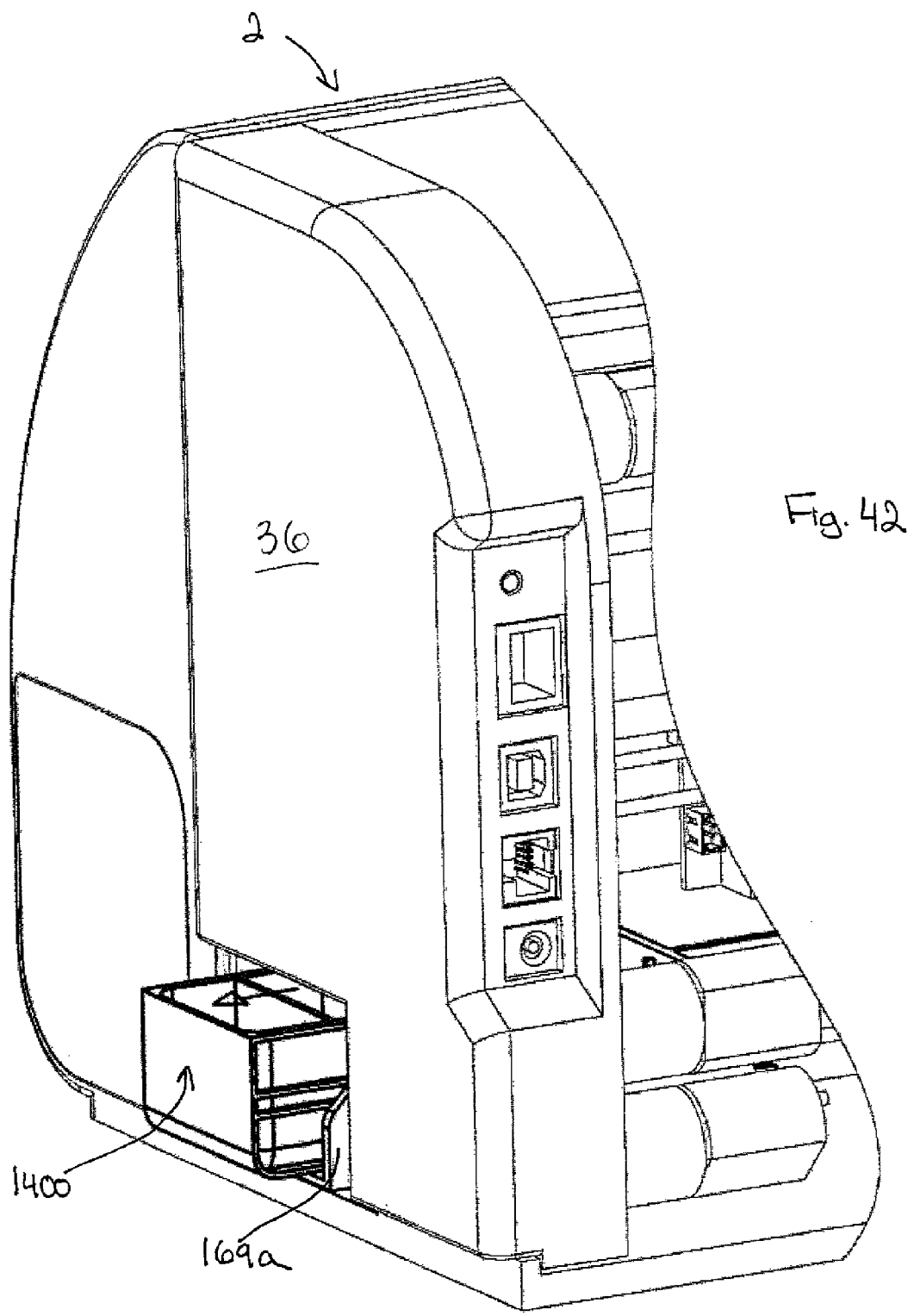
FIG. 42 is a partial perspective view showing a medication container being ejected from the medication dispensing and control unit.

The 6 o'clock position of the rotary drum is the working position associated with dispensing of the medication from a cassette and loading the same into a particular medication container shown as 1400 in FIGS. 40 and 42. There are several distinct aspects of the rotary drum that allow individual cells of the medication cassette to be dispensed by gravity into the medication container. This cell by cell dispensing allows effective counting or confirmation of the medication as it falls from the cartridge supported by the rotary drum to the receiving medication container 1400 that preferably also includes individual cells or groups of cells. The rotary drum 40 includes baffles 1420 that in the preferred embodiment form a ¾ extension of each receiving slot to partially cover a row of cells. ¼ of the baffle not covering one cell of the row allows dispensing of that cell merely by withdrawal of the cartridge to automatically expose that cell. The remaining cells of the row are covered.

Figure 41:
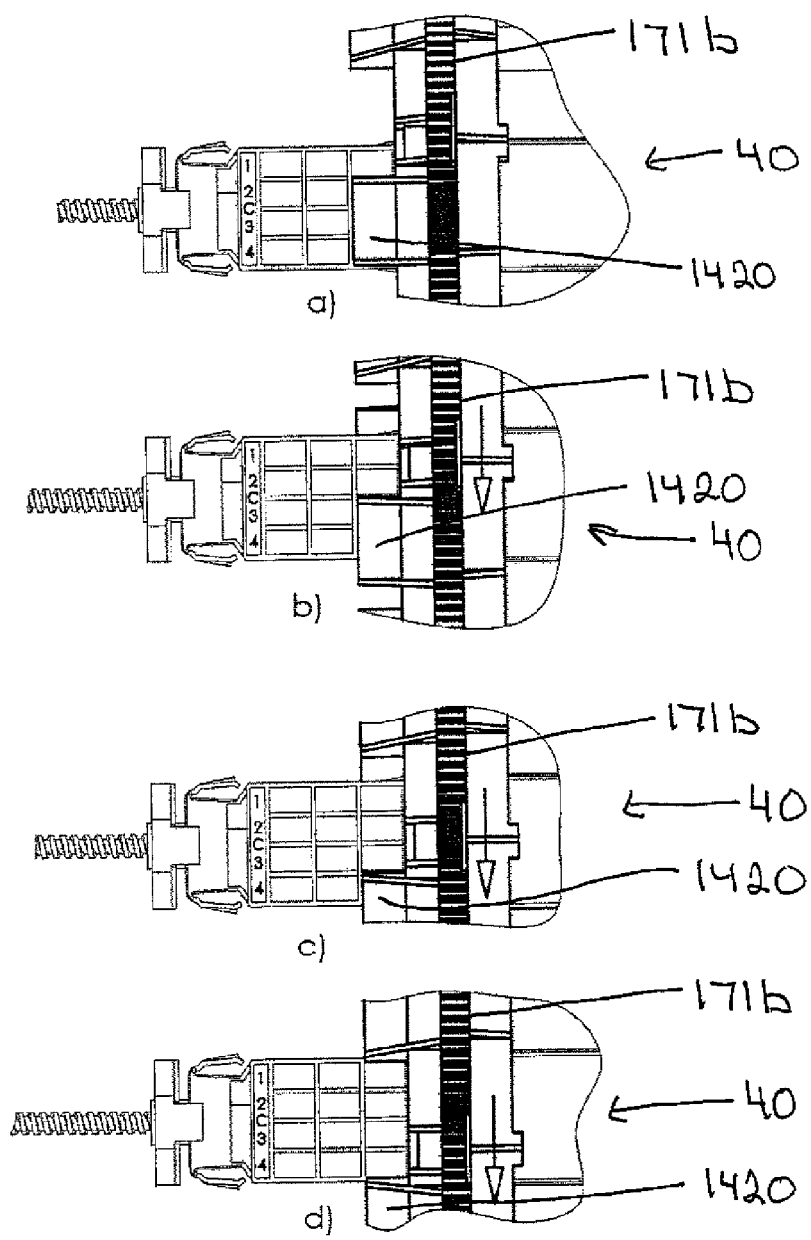
FIG. 41 shows a series of positions of the baffle for dispensing of medications.

To allow dispensing of the additional cells of the row the baffle member 1420 is progressively moved to expose the cells of the row. This movement of the baffle is possible in that the drum is a two part drum and the second part includes the baffle members and is partially rotatable relative to the body of the drum and rotatable relative to the received medication cassette. Basically the opposite end of the drum is locked or held against rotation and the baffle end of the drum is then rotated to cause rotation of the baffle and the exposure of the next cell of the cartridge. The system preferably has previously determined or confirmed the number of cells per row and thus if there are only two cells the appropriate rotation will occur, whereas in four cells per row a reduced rotation would occur. In this way, movement of a row of the cassettes to the dispensing position as shown in FIG. 41*a* allows at least one cell of the cassette to be open as the baffle does not cover all cells. This is the preferred arrangement although the baffle could cover all cells initially however the amount of rotation of the end of drums having the baffles relative to the locked drum would have to increase.

To dispense medication one end of the drum is locked. The opposite end of the drum having the baffles is rotated such that the baffle at the 6 o'clock position is progressively rotated to expose the cells of the row. Release of the baffle will cause the spring member 1450 (FIG. 40) to again realign the baffles with the drum. Appropriate stops are provided between these components to bring the baffles back to the initial position. These stops are not specifically described. Once the baffle is realigned, the lower extractor 1700*a* will then move the cartridge to position the next row of cells for dispensing and the process is repeated. As can be appreciated, the carriage for the receiving medication container 1400 is also accurately controlled and will position the container such that the medication being dispensed falls by gravity into the appropriate cell of the medication container. In this way a series of pills can be dispensed, for example the medication for a particular user for a particular day can all be received in the container 1400 and each medication is provided in a separate cell and perhaps has a time designation for taking of the medication.

FIGS. 37, 37*a*, 38 and 39 show the gravity feed of the pills as they are being dispensed into the medication container 1400 and a light beam is positioned across the dispensing gap 1429 (FIGS. 37 and 38) to effectively detect the medication as it passes through and into the container 1400. This provides accurate tracking and control of the medication from the loading of the cassette through to the individual dispensing of pills into the receiving medication container 1400.

The locking of the rotary drum 40 in a desired position to allow partial rotation of the baffle members 1420 is shown in FIGS. 8 through 12 where the drum locking mechanism 1800 cooperates with the locking slots 1810 associated with the rotary drum and provided on one end of the rotary drum adjacent the support member 34. The locking mechanism 1800 includes a taper-shaped plunger 1812 which is inserted within the locking slots 1810 and this provides effective alignment of the drum and simplifies the accurate positioning of the drum. The locking mechanism 1800 is moved to a release position by the motorized carriage 169*a* for the medication container 1400. The carriage 169*a* when the drum is to be rotated moves the plunger 1812 to a release position against a spring bias of the plunger. The carriage 169*a* is moved to a release position for example to position the container 1400 for receiving pills and the plunger 169*a* under its spring bias will lock the drum. The tapered plunger effectively accurately locates one of the medication cassettes at the 6 o'clock position and locks the drum such that the other end of the drums with the baffle members can effectively be partially rotated against a spring bias of the drum for dispensing of medication in the individual cells.

FIGS. 33 to 39 show movement of the top and bottom extractors used to pull or push the cartridges in and out of the sleeves. These extractors are movable relative to the drum 40 and can be positioned adjacent the drum to engage or grip the end of the medication cassette. The medication cassette is rotated into the finger' gap of each extractor such that there is a top portion 1700 and an L-shaped hook 1702 that is received into gap 1710 of the cartridge. The spring arms are released after the core has been engaged by the extractor. The core is then free to be withdrawn to either allow for the visual inspection of the medication in the individual cartridge at the 12 o'clock position or the movement of the cartridge for dispensing a medication at the 6 o'clock position. The extractors also serve to return the cartridge to the fully received position after the particular process has been completed. Rotation of the drum will then effectively rotate the ends of the cartridge out of the engaging members of one of the extractors and the next cassette is appropriately rotated into engagement with the extractor. The extractors are linked by a gear train but move in opposite directions. With this arrangement only one extractor is functioning at any given time. This provides a simple approach where the extractors are basically in a fixed position in the vertical plane and are movable horizontally typically by a screw drive arrangement.

The overall function of the system 2 has been described however the specific mechanics thereof have not been described in detail. The following will discuss more details of the structure and the control of the different components.

Figure 5:
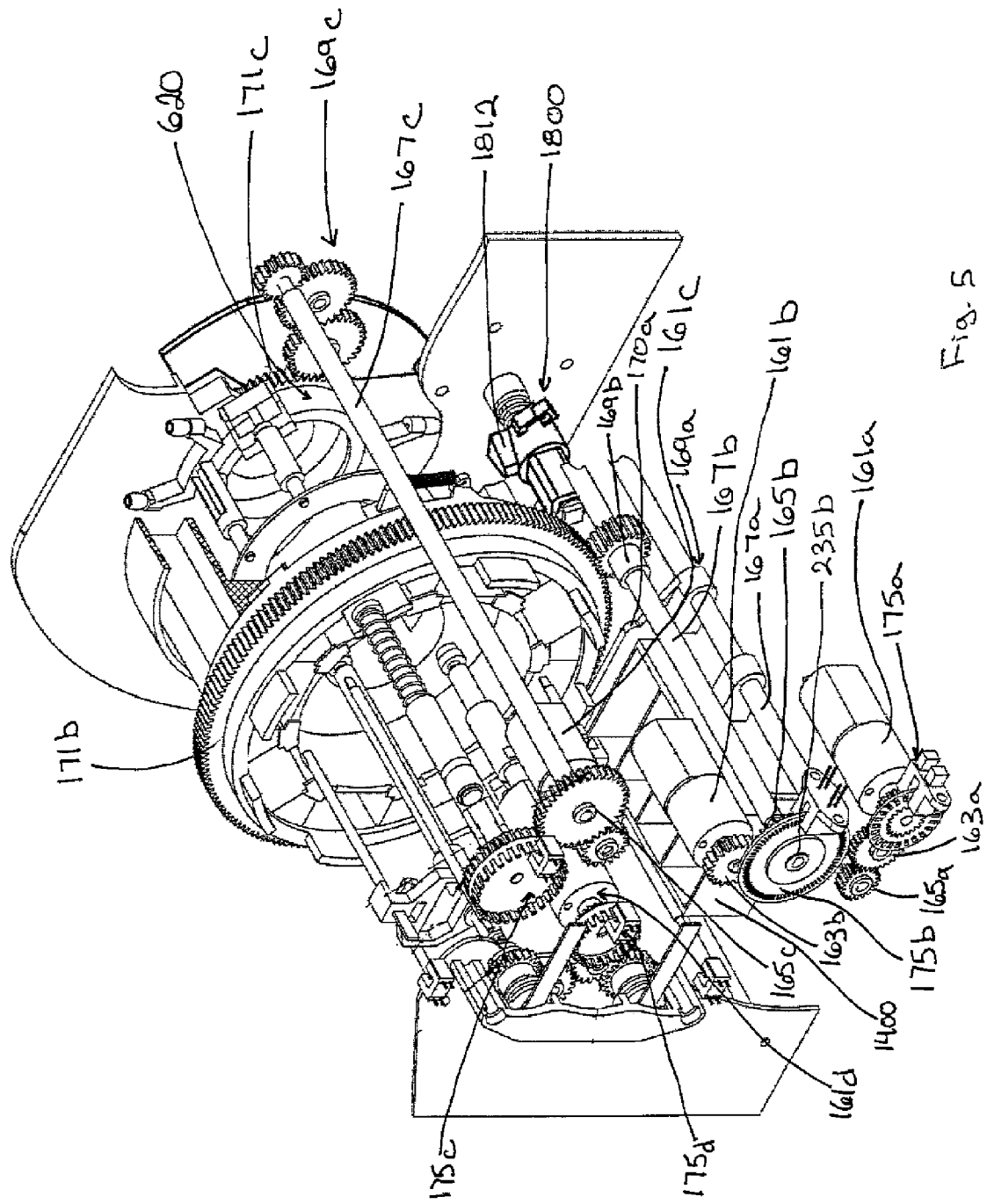
FIG. 5 is a partial perspective view showing the main moving components of the medication dispensing and control unit.

As shown in FIG. 2, the rotatable drum 40 is supported by the end support 34 and the metal support member 60. The metal support member 60 also includes four motors 161*a*, 161*b*, 161*c* and 161*d*. Motor 161*a* as shown in FIG. 5 controls the carriage 169*a* associated with the medication container 1400. As can be seen, the carriage motor drives gear 163*a* that rotates gear 165*a* associated with the screw shaft 167*a*. The carriage 169*a* moves along the screw shaft 167*a*. In this way the medication container 1400 moves essentially the full length of the system 2. The carriage 169*a* includes an end face 170*a* that can be moved to shift the V-shaped plunger used to lock the drum to a clear position. When the carriage is not present the V-shaped plunger 1812 is then free to move and engage the locking slots 1810 of the drum 40.

Motor 161*b* controls rotation of the rotary drum. Drive gear 163*b* drives a gear 165*b* on the drive shaft 167*b* and eventually drives gear 164*b* which rotates the large ring gear 171*b* of the drum. Gear 165*b* includes drive lugs 237*b* that drive surfaces 239*b* of a drive member 241*b* secured to drive shaft 167*b* (see FIGS. 14 and 15).

Motor 161*c* includes a drive arrangement for controlling rotation of the cam 620. This drive train includes gear 163*c*, gear driving shaft gear 165*c* which in turn drives shaft 167*c* and through a drive train 169*c* drives the cam gear 171*c*. In this way accurate positioning of the rotatable cam 620 is accomplished. Motor 161*d* effectively controls the pair of extractors and additional details of this will be provided in the subsequent drawings. Each of the motors includes opto couplers 175*a* through *d* to accurately track the position of the drives.

Figure 6:
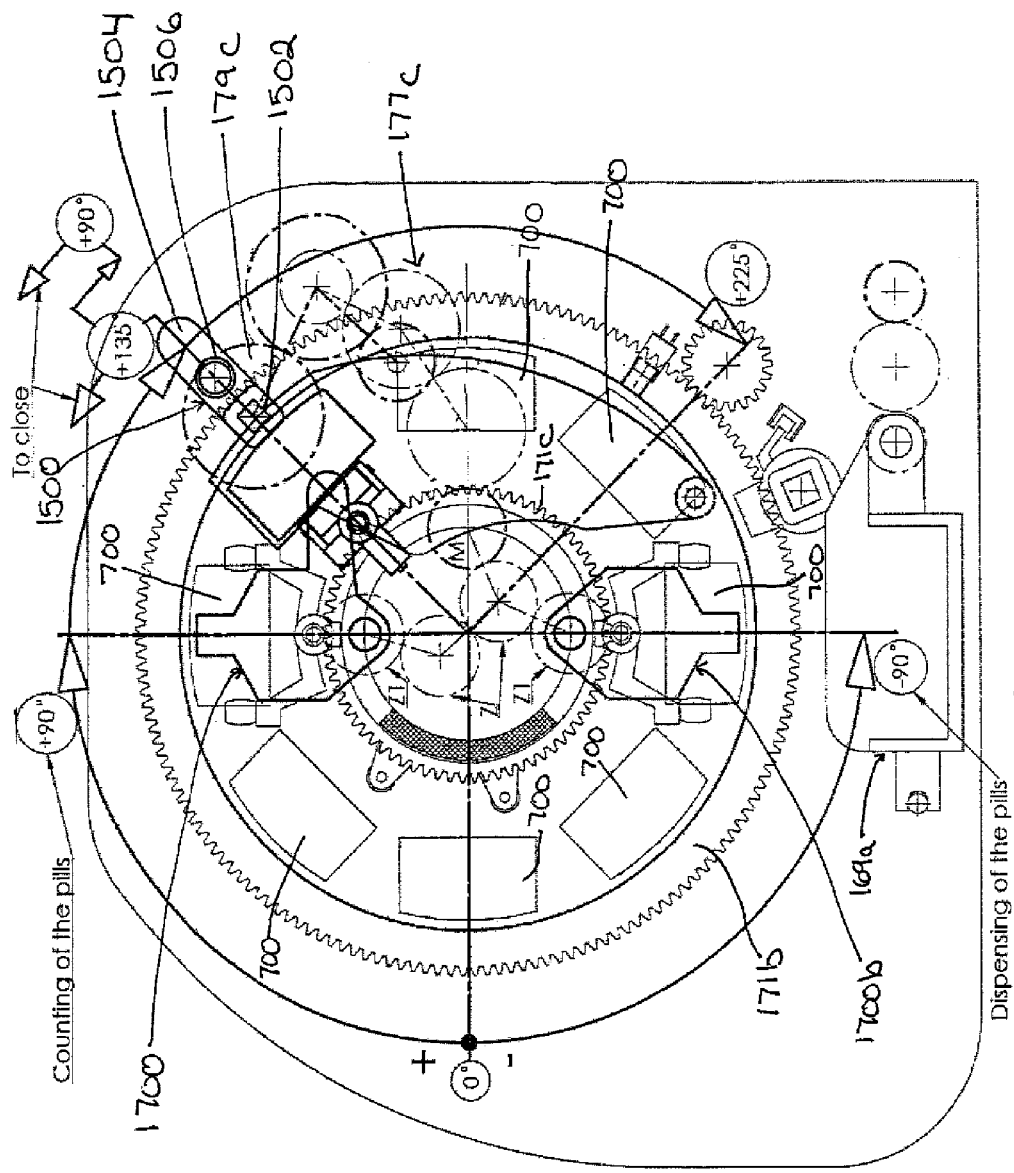
FIG. 6 is an end view of the medication dispensing and control unit showing various components in an initial position.
Figure 7:
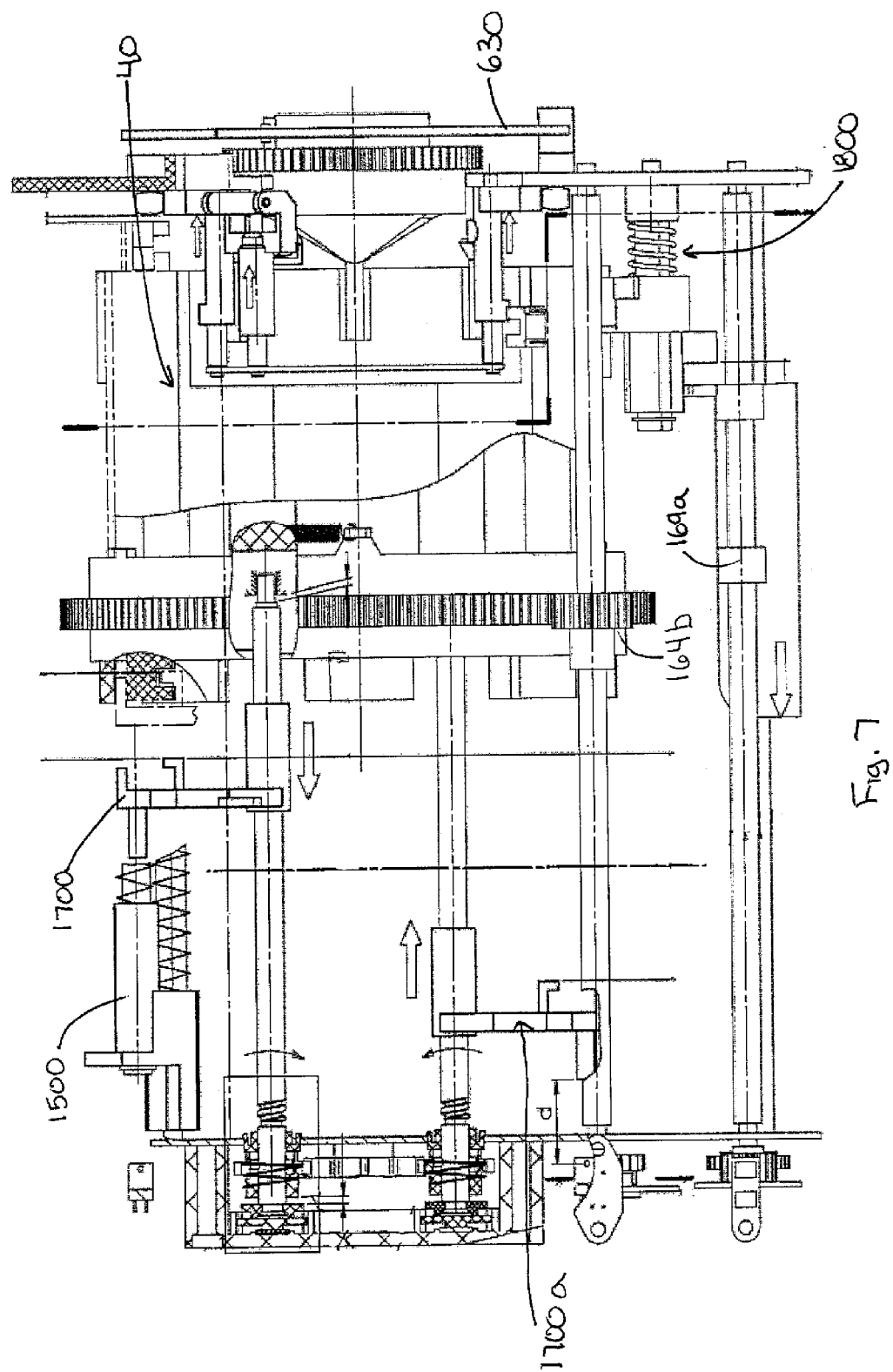
FIG. 7 is a side view of the medication dispensing and control unit showing the operation of upper and lower extractors and upper and lower sliders.

The rotatable cam 620 and its drive gear 171*c* are also shown in FIG. 6. The drive gear 171*c* is connected via a gear train 177*c* to control the position of gear 179*c* and the ejector arrangement 1500. Gear 179*c* includes the ejector slide shaft 1502 that supports the ejector arm 1504 having the ejector plunger 1506 at an end thereof. Rotation of gear 179*c* causes the position of the ejector plunger 1506 to change. The gear train 177*c* has a four to one ratio relative to the cam drive gear 171*c* and control of 171*c* can cause the ejector plunger 1506 to rotate from the position shown in FIG. 6, 180 degrees to position the ejector for receiving of a cassette and also positioned for ejection of a cassette. Basically the ejector arrangement 1500 is controlled to allow rotation of the ejector plunger 1506 to the clear position shown in FIG. 6. This provides additional room for other functions to be carried out essentially by the extractors to one side of the rotatable drum. As will be further described, the motor for the extractors is also used to drive the ejector and to control the position and provide a stop surface for the ejector and to assist in the ejection of the cassette from the rotary drum.

Figure 4:
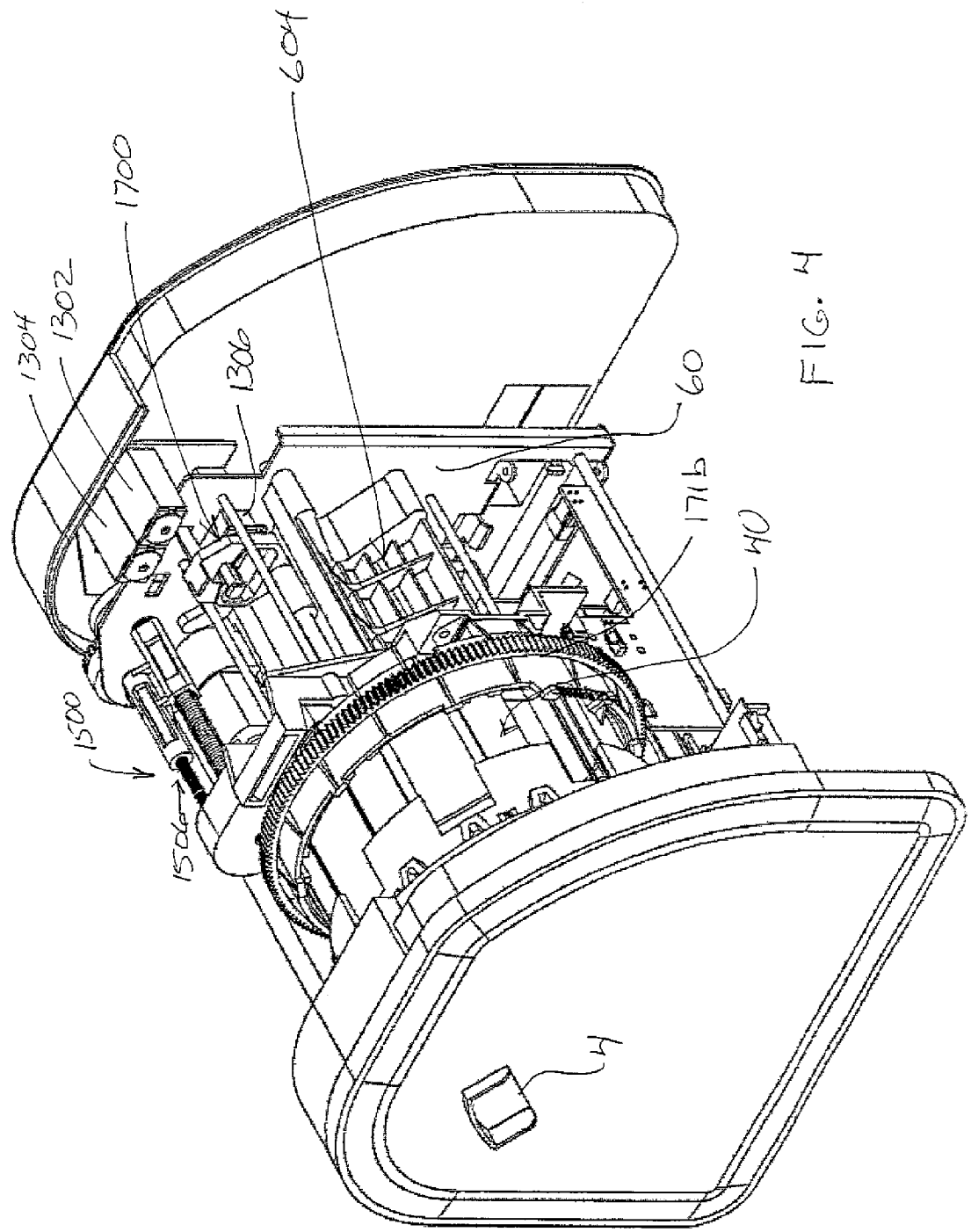
FIG. 4 is a further perspective view showing additional components of the medication dispensing and control unit.

Returning to FIG. 2, it can be seen that the metal support member 60 supports the drive motors 161*a* through *d* and also supports a structure which effectively supports the drum. Additional details of the position of the motors are illustrated in FIG. 3*a* and FIG. 4. As shown in FIGS. 2 and 3, the ejector plunger 1506 is supported on an arm 1504 and includes a spring bias 1508 for urging the ejector arrangement 1500 towards the metal support plate 60 when the ejector arrangement is rotated to an operating position during loading or unloading of a medication cassette.

Figure 8:
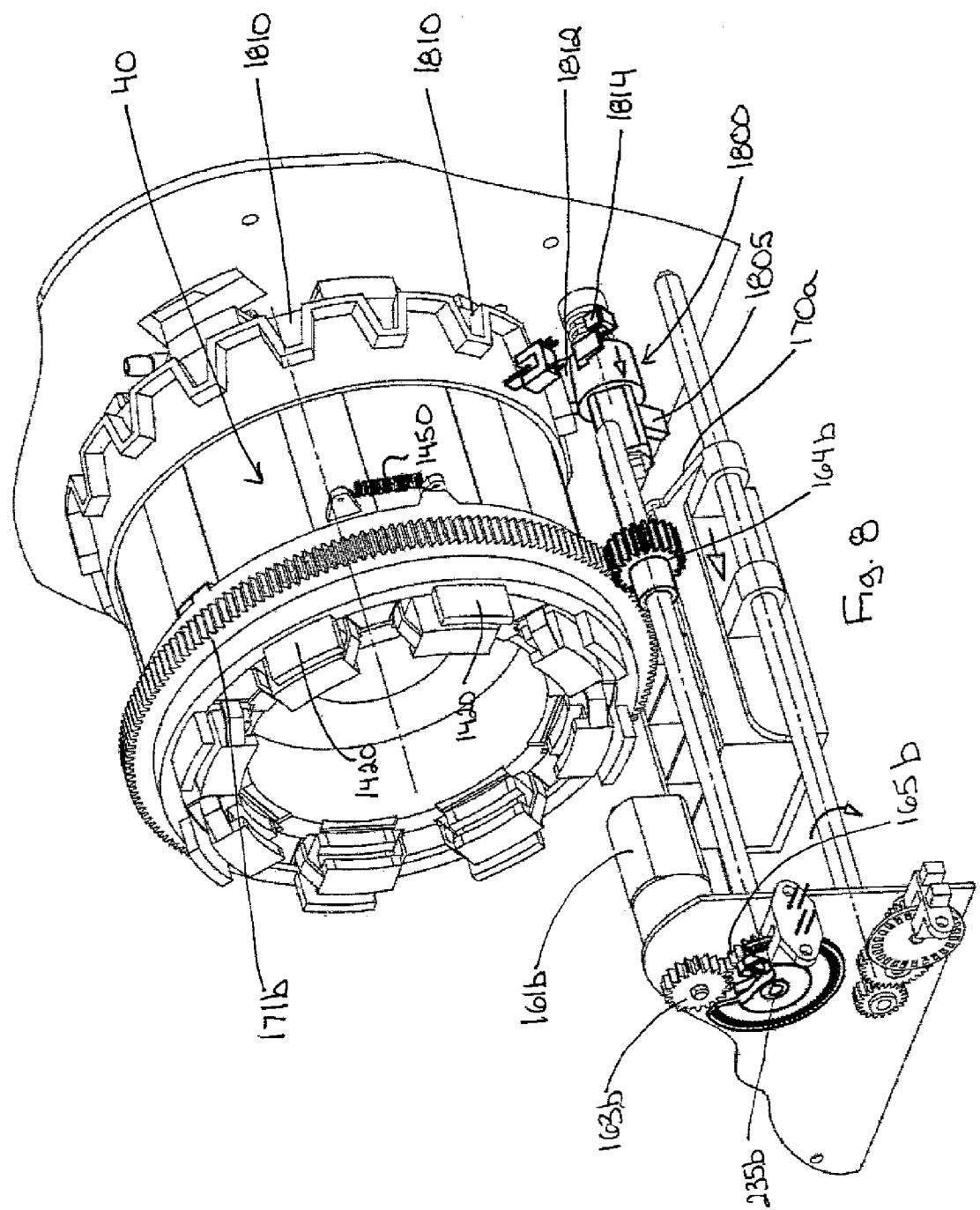
FIG. 8 is a partial perspective view showing the rotatable drum of the medication dispensing and control unit and the drive and lock arrangement thereof.

FIG. 8 shows the relationship of the carriage 169*a* with the drum lock mechanism 1800. The end 170*a* of the carriage 169*a* is movable in the depth of the device to strike the downwardly extending arm 1805 of the drum lock mechanism 1800. In FIG. 8 the drum lock mechanism 1800 is shown in an engagement position locking the rotatable drum 40. The drum includes a series of locking slots 1810 for locking of the drum in various positions. As shown in FIG. 8 the drum lock mechanism 1800 includes the plunger 1812 received in one of the locking slots 1810. The carriage 169a is controlled by the motor 161b to effectively move the drum lock mechanism 1800 to a release position by forcing the carriage 169a to move to the right and move the drum lock mechanism 1800 to a release position thus freeing the locking plunger 1812 from one of the locking slots 1810.

With the right end of the drum 40 locked as shown in FIG. 8 the motor 161b is capable of rotating the drum ring gear 171b to control the position of the baffles. The ring gear 171b can be partially rotated on the drum 40 and this rotation is accommodated by the bias spring 1450. This essentially allows dispensing of pills one at a time as will be subsequently described. It also allows sequential scanning of cells at the 12 o'clock position.

The stop arrangement 1800 also includes a stop sensor 1814 to indicate whether the stopper arrangement 1800 is in an engaged position or a release position. Additional details of the stop arrangement 1800 are shown in FIGS. 9 and 10.

Figure 9:
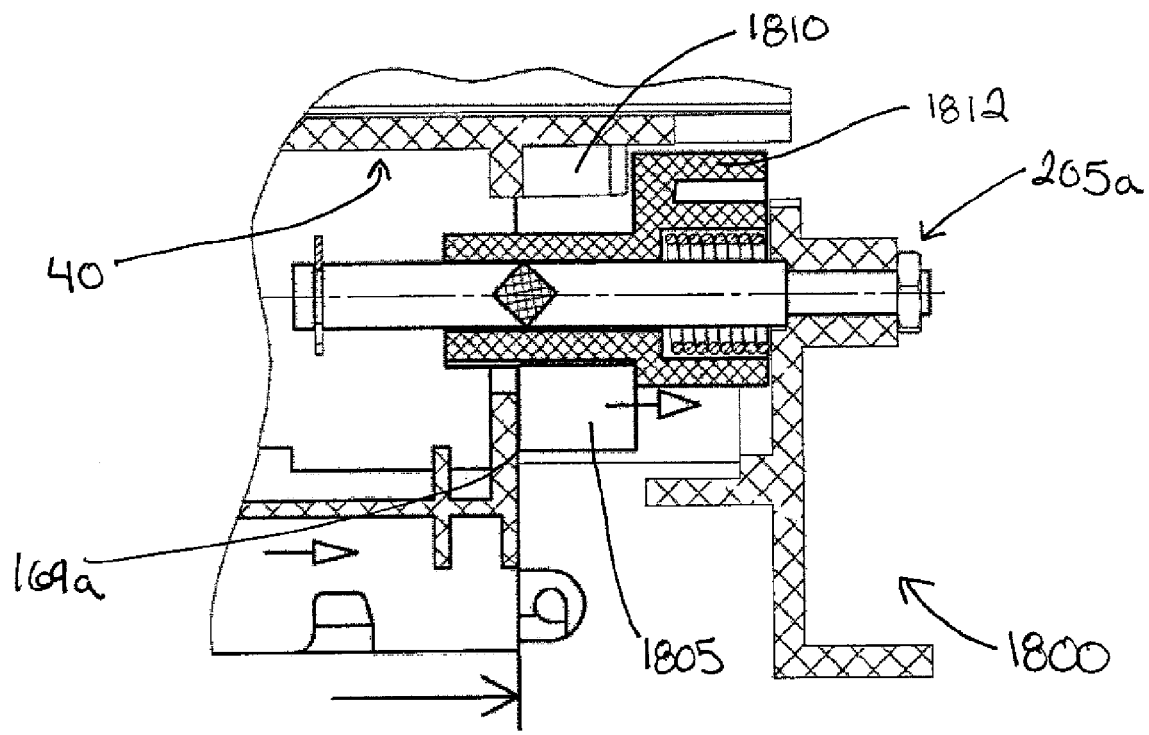
FIG. 9 is a partial section view showing a locking arrangement for the rotatable drum taken along line G-G of FIG. 13 with the drum rotating.
Figure 10:
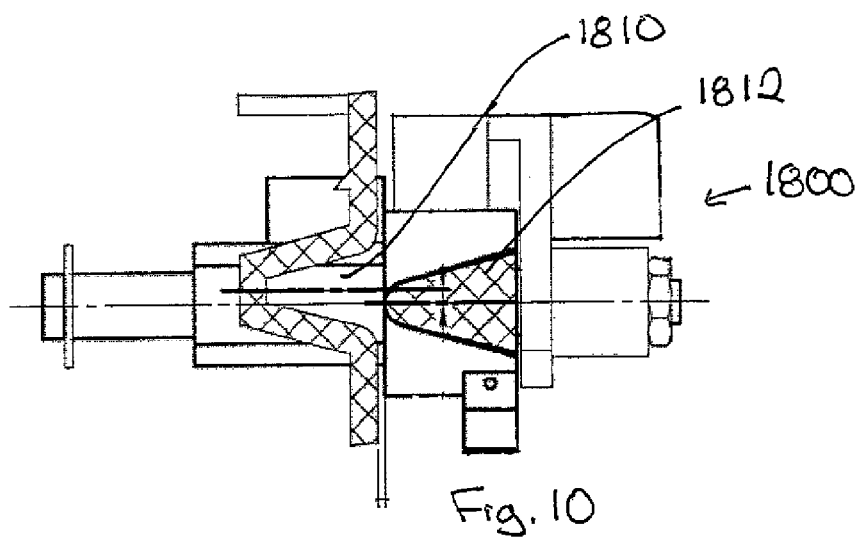
FIG. 10 is a sectional view taken along line H-H of FIG. 9.
Figure 11:
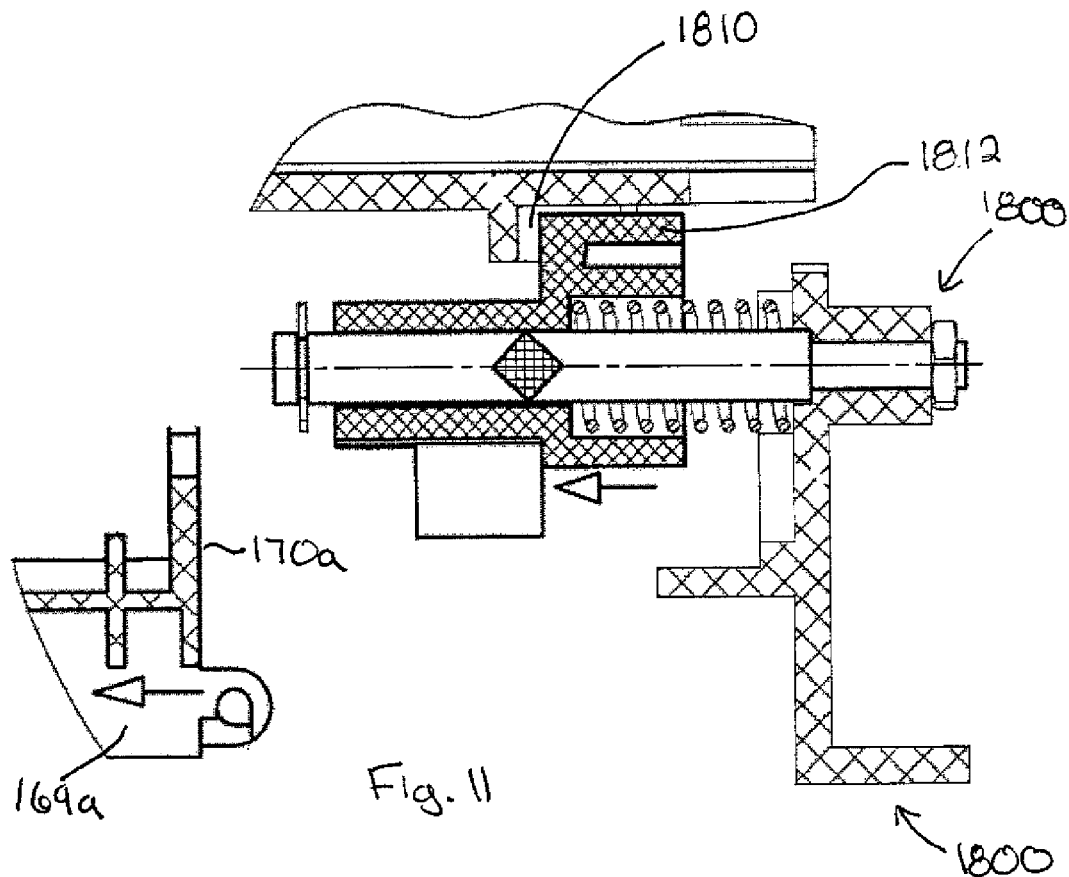
FIG. 11 shows further details of the locking mechanism and is a sectional view taken along line G-G of FIG. 13 with the drum locked.
Figure 12:
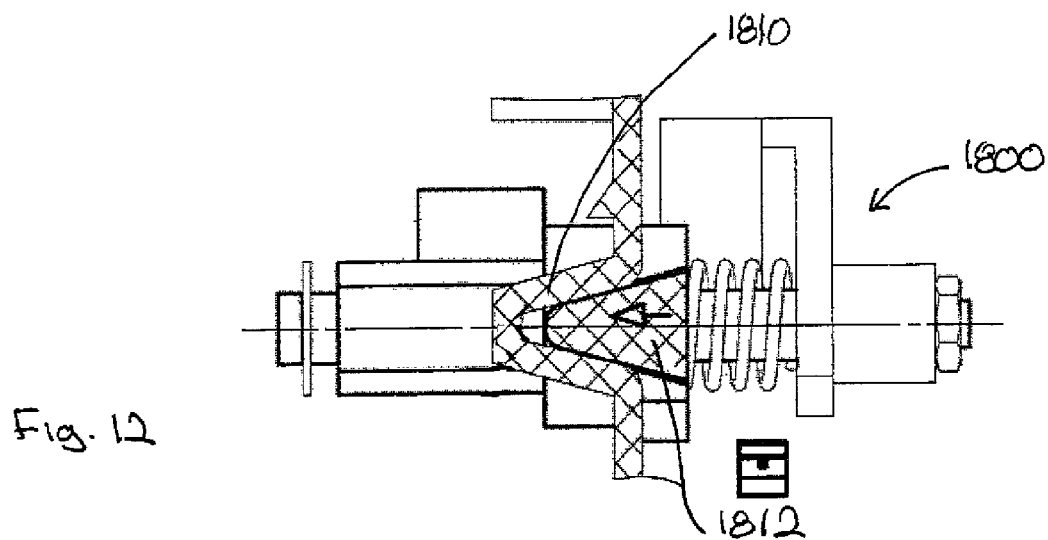
FIG. 12 is a sectional view taken along line I-I of FIG. 11.

In FIG. 9 the drum lock mechanism 1800 is shown with the stopper plunger 1812 in a position clear of the locking slot 1810 of the drum 40. The carriage 169a has moved the drum lock mechanism 1800 to the release position. The motor 161c for the rotary drum 40 basically tracks the position of the drum using the opto coupler however the precise position thereof can vary due to tolerances and wear, etc. To overcome or mitigate these variances, the stopper plunger 1812 is V-shaped and serves to cause partial rotation of the drum to effect exact positioning thereof relative to the drum lock mechanism 1800. This is partially shown in FIG. 10 where the drum has been stopped but is not perfectly aligned with the stopper plunger 1812. The drive of the motor 161c accommodates a certain degree of rotation of the drum from a given position to an aligned position. Release of the stopper lug 1812 to engage the locking slot 1810 on the drum will cause a correcting rotation of the rotary drum to precisely locate the drum in the desired position aligned with the stopper plunger 1812. The v-shaped plunger 1812 effectively acts as a cam and causes the correcting rotation. This correcting rotation can be appreciated from a review of FIGS. 11 and 12 where the v-shaped plunger has now been fully received within the locking slot 1810. A partial rotation of the drum has occurred.

Figure 14:
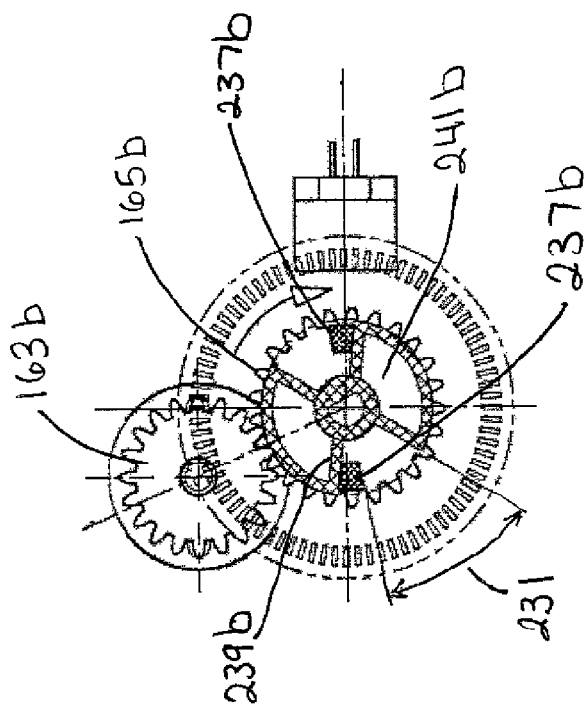
FIG. 14 shows details of the drive for the rotatable drum and is a sectional view along line D-D of FIG. 7.
Figure 13:
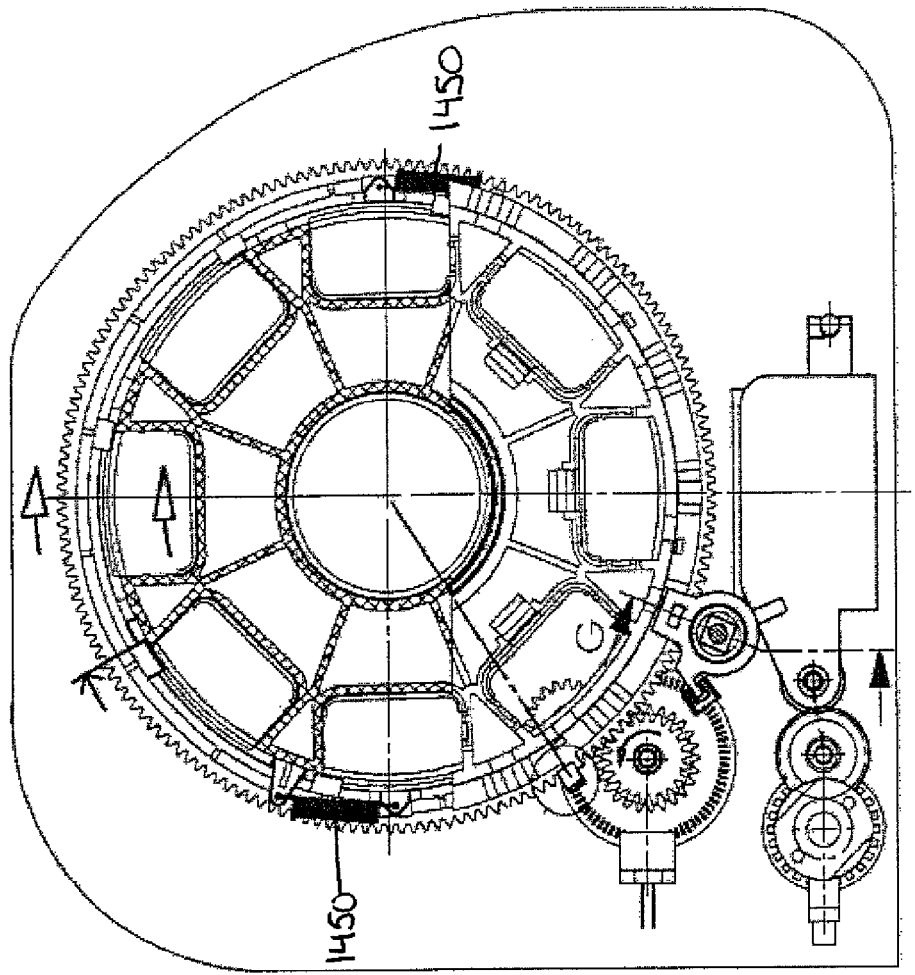
FIG. 13 is a sectional view of the rotatable drum along line C-C of FIG. 7 and shows the drive mechanisms for the rotatable drum and the medication container.
Figure 16:
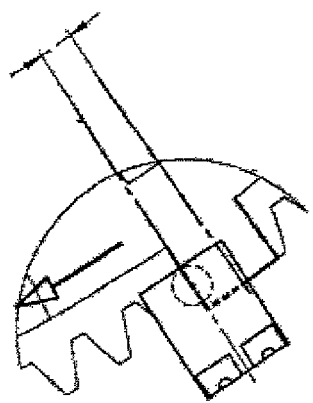
FIG. 16 shows details of the sensing arrangement for the position of the rotatable drum and is an enlargement of Detail F of FIG. 13.
Figure 15:
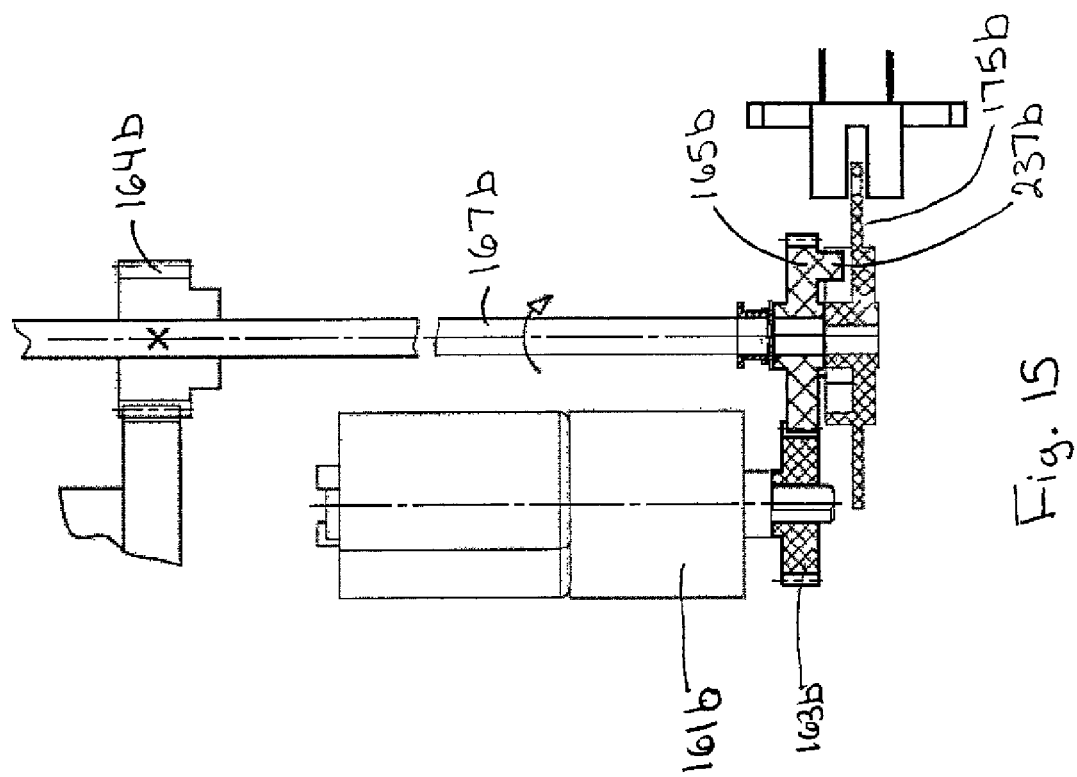
FIG. 15 shows further details of the drive for the rotatable drum and is a sectional view along line E-E of FIG. 14.
Figure 18:
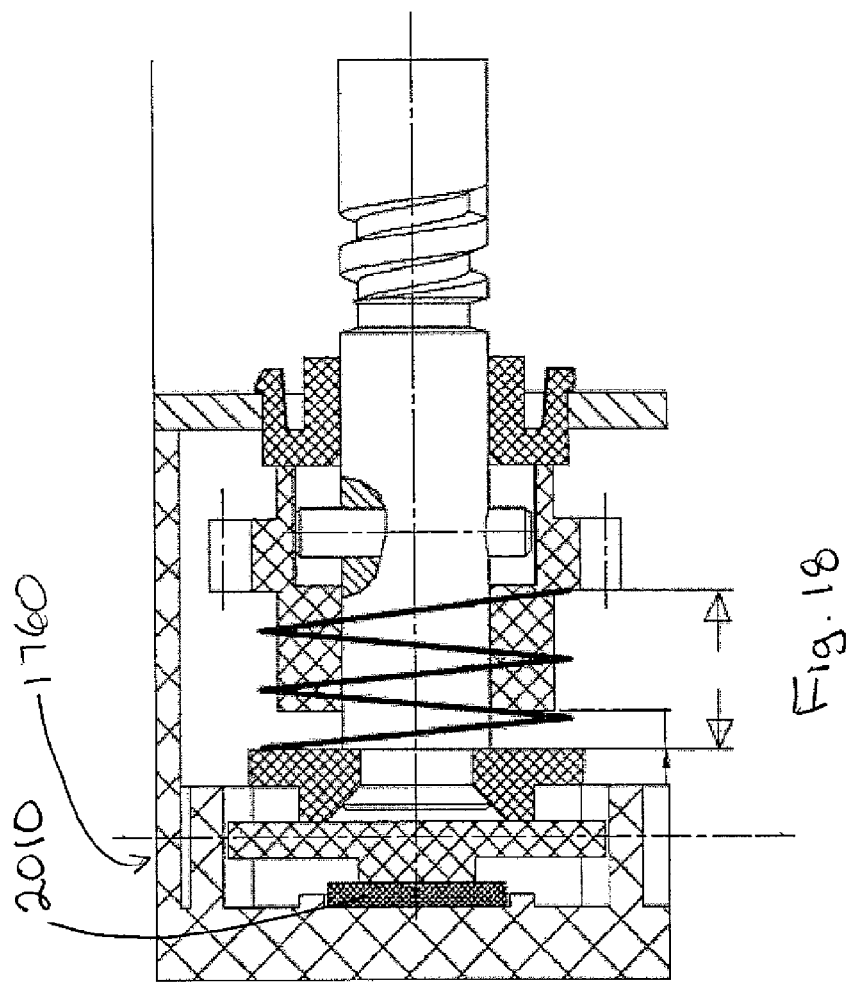
FIGS. 17 and 18 show details of a pressure sensing arrangement for a drive shaft of the unit with FIG. 18 showing Detail A of FIG. 7.
Figure 17:
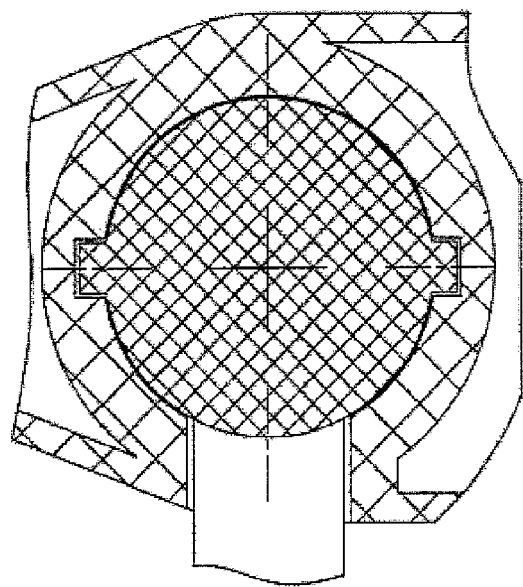

FIGS. 13, 14 and 15 illustrate a particular drive arrangement for the rotary drum that includes the capability of the drum to partially rotate in the opposite direction. This is shown as an idle angle of rotation 231 in FIG. 14. Motor 161b drives the drive gear 163b. This in turn drives the gear 165b having integral drive lugs 237c. Gear 165b is freely rotatable on shaft 167b. Drive lugs 237b contact drive surfaces 239b of drive member 241b secured to drive shaft 167b. The opto coupler accurately positions the drum in a stop position but there may be the requirement to additionally locate the drum by means of the stopper lug. The tolerance angle 231b where the lugs 237b can separate from the drive surfaces 239b within the drive member 241b to allow the limited movement of the rotary drum 40 to effect precise alignment of the drum with the extractors or other working positions of the drum. Thus the v-shaped plunger 1812 will cause drive lugs 237b to move relative to the surfaces 239b of drive member 241b during precise alignment of the drum on the drum lock mechanism 1800. This drive arrangement is also shown in FIG. 15. The tolerance or limited clutch type drive arrangement overcomes the precision that might otherwise be necessary by the drive motors and the drive train. The opto coupler tracking the drive train does provide accurate initial positioning of the drum however the additional limited rotation of the drum is accommodated by the tolerance angle. Basically the drum is always rotated to a position such that the correction can occur in one direction. This basically separates the drive train from the motor which would otherwise lock the system due to the relatively high gear ratio. As can be appreciated this provides a simple and effective mechanism for accurately locating the drum and locking the same to allow dispensing of pills, checking of medication cassettes for the appropriate number of pills, as well as the insertion and removal of cassettes. All of these functions require accurate positioning at the particular work positions of the drum and a series of locking slots 1810 provided on the drum 40.

Figure 19:
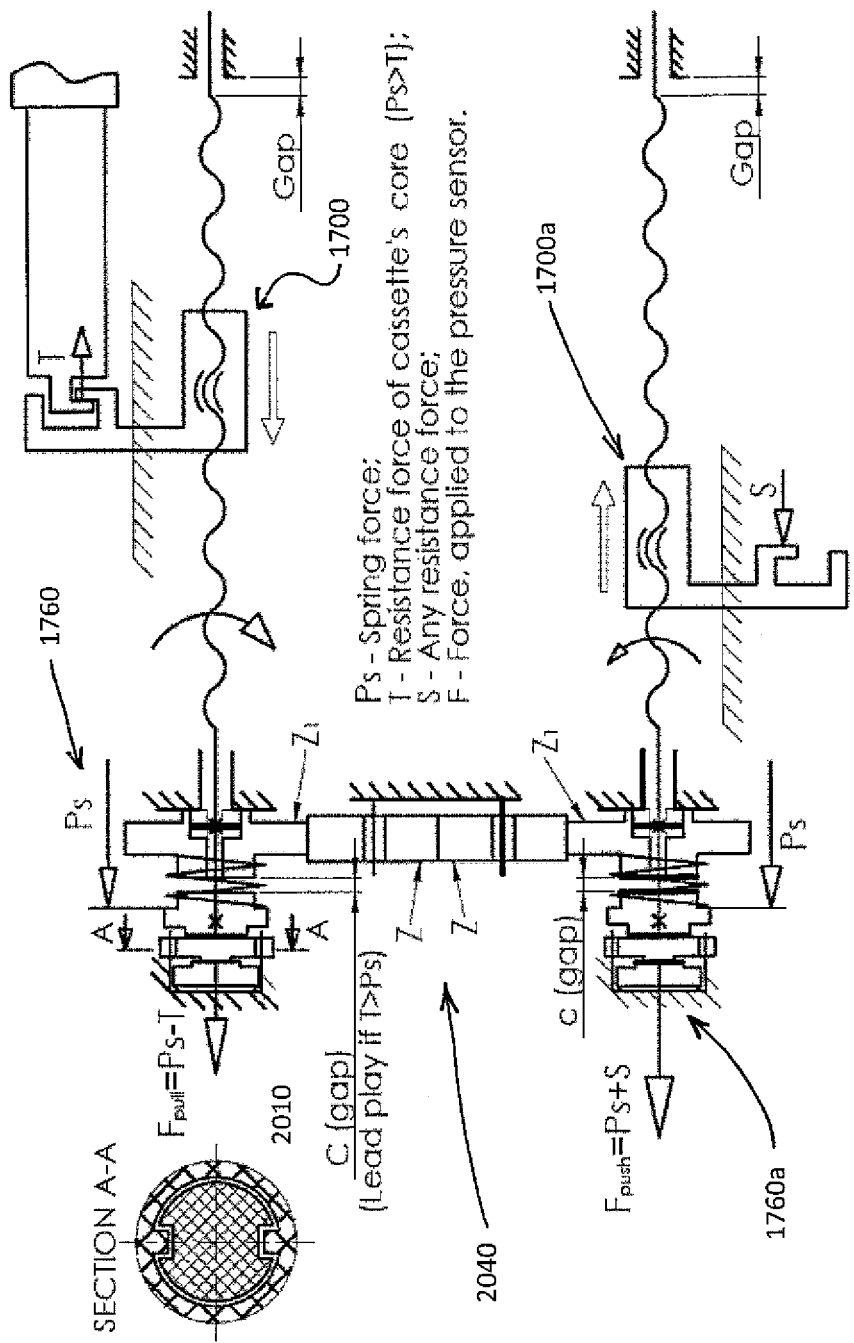
FIG. 19 is a partial schematic view showing the drive arrangement for the upper and lower extractors of the medication dispensing and control unit.

FIG. 19 shows the drive arrangement for the upper extractor 1700 and the lower extractor 1700a. Details are also shown of a pressure sensing arrangement 1760 and 1760a associated with each of the extractors. Each of the upper and lower extractors is slidable along a guiderail system and thus is movable towards or away from the drum. Either the upper extractor or the lower extractor is positioned adjacent the drum prior to rotation of the drum to bring a cassette to the 12 o'clock position or the 6 o'clock position respectively. As shown in FIGS. 33 and 34 the upper extractor is controlled by the worm drive shaft 2200 and this worm drive shaft 2200 includes a spring bias 2202 forcing the drive shaft towards the right and the spring force is also exerted against a pressure sensor 2010. The upper extractor 1700 with its actuating surface 1702 received within a cassette cavity 1710 will have some tolerance variation to effectively allow the end of the cassette to rotate and engage the extractor. This tolerance variation, if not accounted for, may cause problems and reduces the accuracy of the position of each row of cells relative to the drum and to the baffle to allow scanning or dispensing of individual cells. To overcome such tolerance variations the pressure sensor 2010 basically has a spring force PS exerted on the pressure sensor at times when the extractor is not withdrawing the cartridge from the medication cassette. As can be appreciated, when the screw drive of the extractor is rotated to cause partial withdrawal of the cartridge from the cassette, any tolerance clearance between the cassette and the extractor is taken up first. Once the extractor starts to pull on the cartridge the cartridge will exert a smaller force T (resistance of the cartridge) in the opposite direction due to the drag of the cartridge. With this arrangement the force sensed by the pressure sensor 2010 suddenly changes and it is this appreciable change in pressure force that is used to confirm that the cartridge is now about to be withdrawn. As the width of the cells is known by the system, the extractor can then be moved the appropriate distance to expose the next row of cells. As previously described, the medication cassette had been inserted in the drum and forced to the right such that the position of the medication cassette within the drum is already known and thus the distance for removal is known. With this arrangement accurate withdrawal of the cartridge is accomplished.

The drive train 2040 and motor 161d are also shown in FIG. 33 and the direction of movement of the upper extractor 1700 relative to the lower extractor 1700a is in the opposite direction. In this way only one of the extractors operates at any given point in time. Additional details of the upper and lower extractors are shown in FIG. 34.

FIGS. 22 through 27 of the drawings exemplify, the particular cooperation between the upper and lower sliders (1360, 1380), the cam 620 and the release of the spring arms 58 of the medication cassette 50 at the 12 o'clock and the 6 o'clock positions. Each of these sliders (1360, 1380) is spring biased against the cam 620 and the cam is rotatable to move the sliders to cause release of the spring arms when the cam moves the sliders towards the rotary drum 40. The cam 620 is controlled by the drive motor 161c and the drive train associated therewith and thus the exact position of the cam 620 relative to the sliders is effectively tracked. The actual movement of the upper slider relative to the spring arms of the cassette is shown in FIG. 23 where it can be seen that the cam has now moved the slider into engagement with the spring arms 58 and thus the cartridge can be pulled into the sleeve and out the other end of the drum. Further details of the action on the sliders are shown in FIGS. 24 and 25.

FIG. 28 shows the additional structure used to essentially release the spring latch when a cassette is ejected. The spring latch automatically provides a catch to maintain a medication cassette when fully inserted into the drum. A spring force is exerted on the medication cassette by the ejector mechanism during insertion into the rotary drum and the spring latch 1100 effectively provides an automatic latch for the medication cassette when properly inserted. If the cassette is not fully inserted, the spring force of the ejector causes the cassette to move outwardly.

The mechanism shown in FIG. 28 is for release of this spring latch 1100 during ejection of a cassette and is actuated by the roller 1156 forcing the spring latch to a clear position.

FIG. 27 shows the further action of the spring latch 1100 when a medication cassette is being inserted into the drum. In this figure the medication cassette is about to engage a cam surface 1102 of the spring latch to push the spring latch upwardly. Once the cassette is fully received the spring latch will move downwardly and thus act as a stop for the medication cassette.

In FIG. 28 the ejector plunger 1506 has been rotated to an operative position and is now engaging the end of the medication cassette. The ejector plunger is itself spring biased and the plunger is compressed within the ejector by the cassette moving and locking with the drum. The position of the ejector plunger 1506 is controlled by the upper extractor arm 1710 engaging arm 1504 of the ejector arrangement. This acts as a stop and allows the plunger to compress. The motor 161c when appropriately driven to additionally cause rotation of the cam 620 will cause rotation of the ejector between the operative position of FIG. 28 to a clear position as shown in the earlier figures.

FIG. 29 shows movement of the ejector plunger 1506 by the upper extractor being driven on its worm drive gear shaft. The ejector slides on its own guide rod 1502 and is driven by the upper extractor arm to eject the medication cassette out of the drum. Typically the cassette will partially extend out of the drum whereafter the user completes the full withdrawal thereof. As can be appreciated, this ejection of the medication cassette occurs when the drum is in the desired position and this position is effectively locked by the locking mechanism previously described. As can be seen in FIG. 29 the cam 620 has caused the actuator to move the spring lock to a release position such that the cassette can be removed from the drum. Additional details of this action are shown in FIG. 30. The cam 620 has also caused the shutter to be open.

Figure 31:
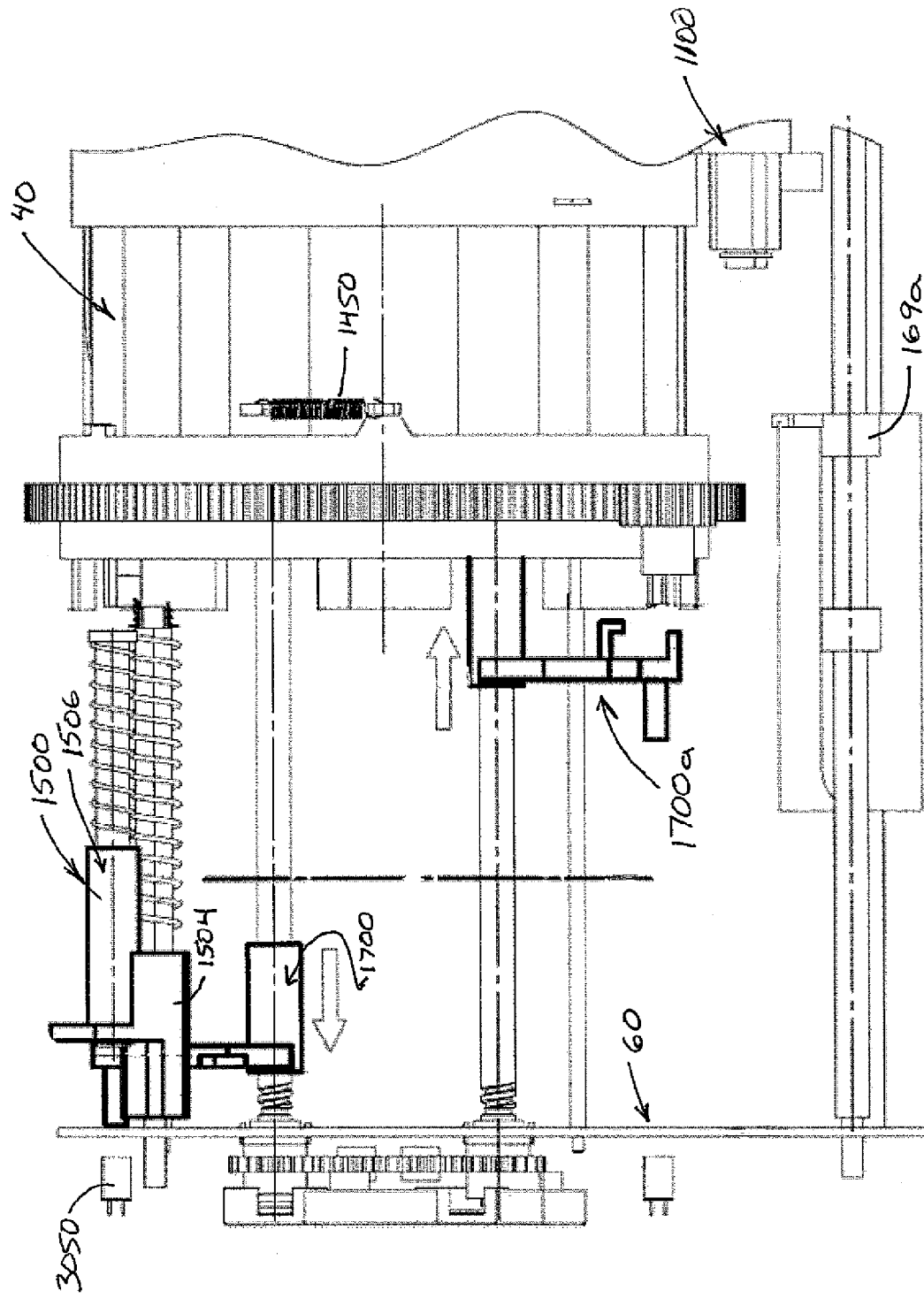
FIG. 31 is a partial side view showing details of the upper and lower extractors and the ejector of the unit.
Figure 32:
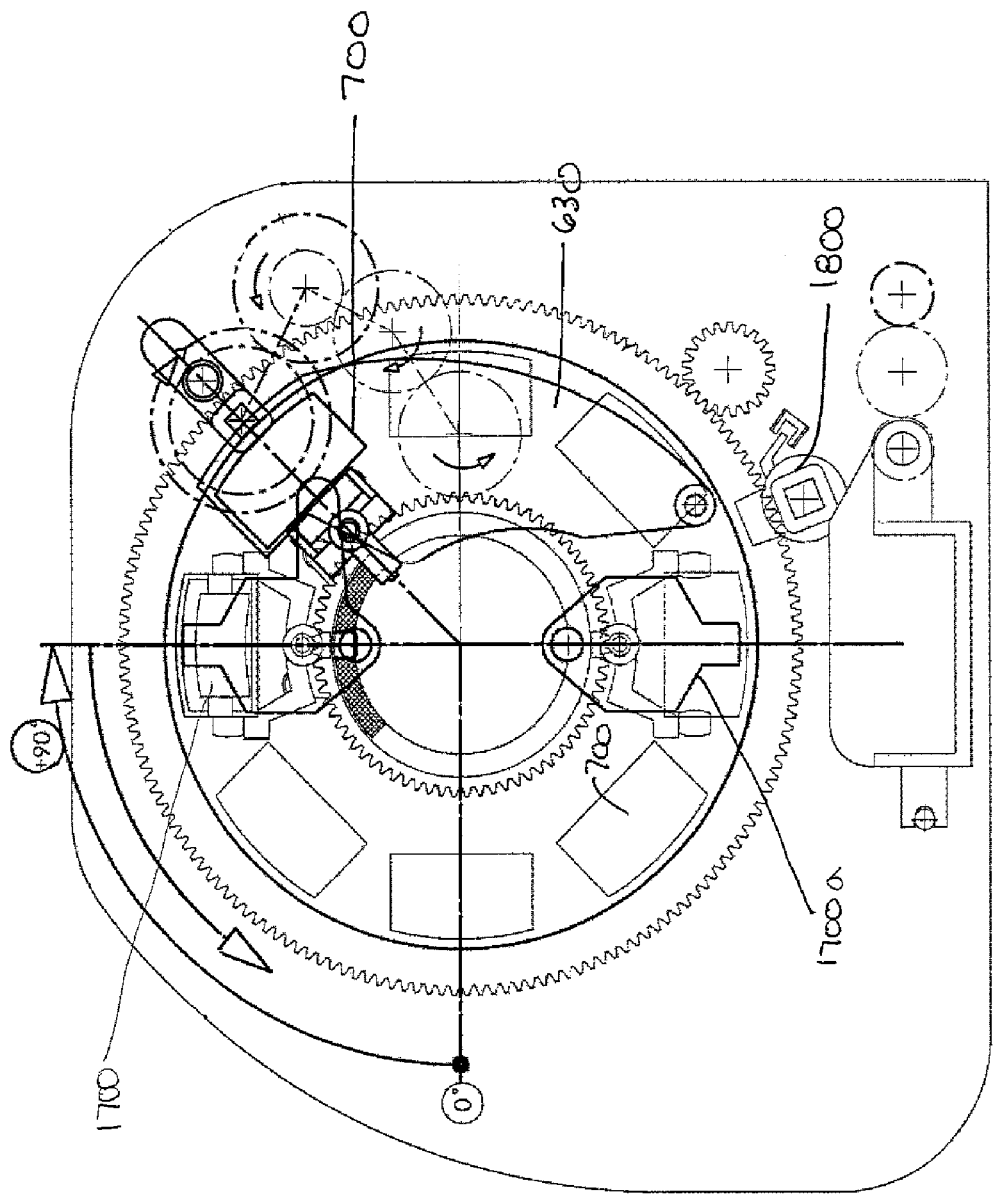
FIG. 32 is an end view showing the mechanism for rotating of the ejector and the rotatable cam between the inoperative position shown to an operative position for the purpose of counting pills.

FIG. 31 illustrates the movement of the extractors and the cooperation of the upper extractor with the ejector arrangement 1500. The ejector has been rotated into an operative position and it includes its own spring bias to move the ejector towards the metal support plate 60 and generally clear of a cassette. The upper extractor would have been moved to a position adjacent the metal support member 60 such that it can engage and drive the ejector arm 1504. The drive of the upper extractor moves the ejector arrangement 1500 towards the rotary drum and positions the ejector arrangement appropriately for either providing a spring bias for the medication cassette during insertion into the rotary drum or for assisting in ejection of the medication cassette from the rotary drum.

FIG. 31 also shows two limit switches 3050 and 3052 which are used to sense the position of the extractors. These sensors are used to control the movement of the extractors and to maintain an assessment of the particular positions thereof. The motor is stopped when one of the extractors is moved to cause actuation of one of these sensors. When one extractor is at a limit switch the other extractor is in a loading position for engaging a medication cassette when aligned therewith.

FIGS. 33 through 35 show the upper extractor withdrawing a cassette in the 12 o'clock position and confirming the medication received within the cassettes. As shown the light emitter transmits a light beam to the mirror positioned over a particular cell and the light passes through the cell, hits a further mirror and can be sensed by the light receiver. As shown in FIG. 3, when a pill is located within the individual cell the light beam is interrupted and thus presence of a pill is confirmed. If the cell is empty the light will pass through the light transmitting bottom portion of the cassette. Two light transmitters are shown and are used for scanning different cells of the medication cassette. The first light emitter can scan the first two cells of a row. To scan the first cell the baffle covers cells 2, 3 and 4. To scan the second cell the baffle is shifted to expose the second cell. If pills are present in cells 1 and 2 the light is blocked. If cell 1 is empty and cell 2 has a pill light received is essentially the same as for cell 1. If both cells 1 and 2 are empty a higher amount of light is received. Scanning of cells 3 and 4 is similar but the second light transmitter is used and the baffle is moved for exposing cell 3 first followed by exposing cells 3 and 4. Other arrangements for scanning of the medication cassettes can be used.

FIG. 34 shows further movement of the cartridge of the cassette and several rows of cells of the medication cassette have already been counted. As can be appreciated the first two rows of cells of the cassette are empty and light would have transmitted through these cells when the individual cells were scanned. Two rows of cells were processed and pills were confirmed as located therein and the fifth row of cells is now being sensed and the light beam is being interrupted by that particular medication. This scanning of the medication can also assess the size of the medication and compare the same versus a provided or predetermined size.

FIG. 35 shows additional details of the medication cassette as it is being withdrawn at the 12 o'clock position for assessment of the contents thereof.

Figure 39:
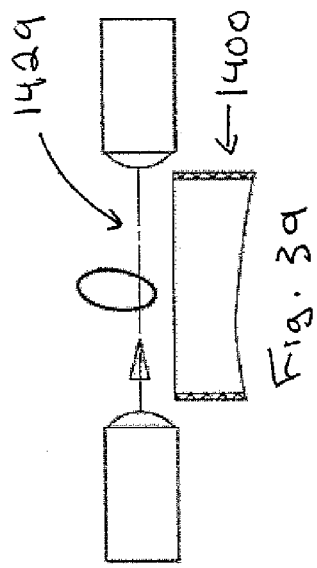
FIG. 39 is a schematic type view illustrating detection of a dispensed pill relative to view B of FIG. 38.
Figure 38:
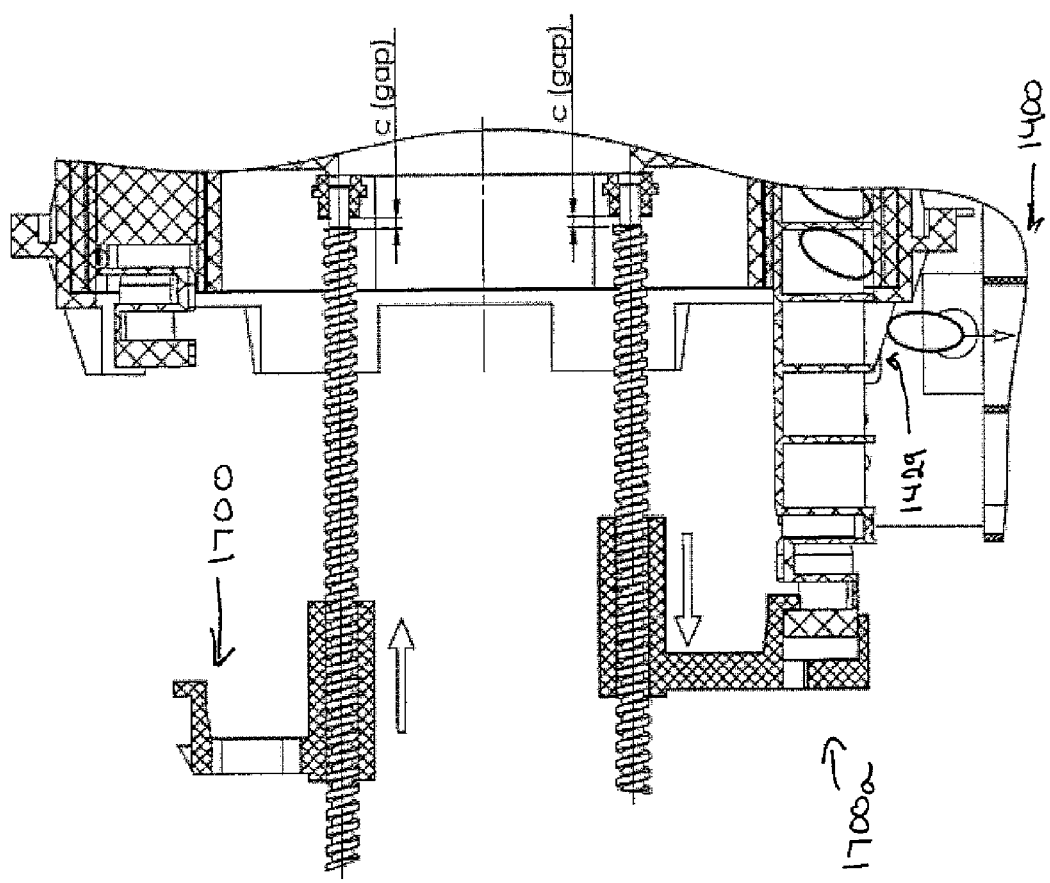
FIG. 38 is a partial side view showing the lower extractor engaging a cassette for dispensing of medication and shows Detail A of FIG. 37.

FIGS. 36 through 41 show details of the dispensing of pills where the lower extractor is partially removing a cassette from the rotary drum. As shown in FIG. 37 the first cell of the medication cassette is effectively opened and the pill is now dropping into the medication container. The pill basically passes through a light passage and a light beam is interrupted as the pill falls into the container. In this way confirmation of the dispensing of the pill is confirmed. The medication container has been appropriately located beneath a delivery chute and receives the dispensed pill. Further details of this are shown in FIGS. 38 and 39. FIG. 40 is a partial perspective view showing the withdrawal of the medication cassette from the rotary drum to allow dispensing of the pills contained in the individual cells.

The rotary drum 40 as previously described is made of two parts that normally rotate together and are maintained at a particular orientation by the spring member 1450. The drum can be locked at the end adjacent the cam 620 and the opposite end of the drum that includes the baffles 1420 can partially rotate to expose individual cells of the medication cassette. Basically when the drum is locked the drive gear 171*b* is partially rotated the appropriate distance to sequentially expose individual cells of a row of cells. Once the pill has been dispensed, the gear is then rotated a further amount such that the baffle is moved to expose the next cell. Views a, b, c and d of FIG. 41 each show this rotation of the baffle 1420 to individually expose cells. As can be appreciated each of these slots of the drum include their own baffle and thus pills are dispensed from the cells of the cassette one at a time. Once all pills of a row have been dispensed into the medication container the drive gear 171*b* is returned and the spring causes the baffle to again assume the normal position (FIG. 41*a*) relative to the locked portion of the drum. The extractor can then pull the medication cassette outwardly to expose the next row of cells. In the embodiment shown the baffle 1420 is positioned to allow the first cell of a row to be exposed and to allow gravity dispensing thereof. The dispensing of the next cell of the row requires movement of the baffle relative to the locked drum.

The present invention includes four motors for driving various components of the system. The rotary cam 620 is used to control the shutter of the system, is used to control the position of the ejector between an operating position and a clear position, is used to cause actuation of the upper and lower sliders, and additionally is used to allow release of a medication cassette from the rotary drum. The motor for the upper and lower extractors not only controls the position of these extractors but it also is used to cause the upper extractor to appropriately act as a stop for the ejector when it is moved into the operating position and is also used to move the ejector to assist in the ejection of the medication cassette from the rotary drum. The motor for the carriage for the medication container is not only used to control the position of the carriage as the medication container but it is also used to control the position of the spring biased drum lock arrangement.

The present arrangement provides effective control of both the loading of medication cassettes for one user as well as confirmation of the contents thereof. The device then provides accurate dispensing of the medication into an appropriate container provided on the carriage. As shown in a number of the drawings the drive for the carriage is also used to allow the container to be removed from the device when it has been appropriately loaded and to allow a subsequent container to be placed on the carriage for loading.

The device includes various sensors and a computer control arrangement for receiving information with respect to the particular medication cassettes, the users and the medication dispensing requirements. The medication cassettes preferably include their own readable information regarding the user and the medication and dispensing instructions. The ability of the system to also receive test results for individual users typically by auxiliary equipment is also beneficial in providing full tracking of the medication dispensing regime and the tests that are received from time to time or on a predetermined basis. This provides an accurate health record for the individual users. Such full tracking of medication dispensed and test results over time is believed to be unique for non-health care facilities. With this system accurate health records are recorded in the home that can assist medical professionals monitor home care and/or assist in diagnostic evaluation if a change in health occurs. Such a change may be the result of failure to follow a predetermined medication regime.

Other features of the system can include automatic reminders to administer non-dispensed items like eye drops, or to book or as a reminder for medical tests, etc.; provide two ways video/audio communications with MD, etc.; and to provide security of operations by allowing access to authorized persons only via fingerprint sensor, by entering code, or other security code or feature.

The device can also be used for dispensing of non medical items where control and/or precision is required.

The ability of the system to receive medication dispensing instructions, track the dispensing and receive test results allows a medical professional or other qualified person to input "What if" options where the dispensing regime can react to the actual measured conditions of the user. Changes in the medication regime can be reported before or after a regime has been changed. The system can accept multiple forecasts or changes that should be acted upon given certain test results. This allows dynamic response on certain possibilities that had been recognized by the advisor and preprogrammed. Various safeguards can be employed including multiple tests, retesting prior to a change or electronic instructions confirming the change by the advisor.

The ability of the system to track, test and preferably adjust or respond to the patient's conditions represents a major shift or change in patient care. The standard of allows seeking medical advice that typically requires further tests can now be superseded to significantly reduce the time required in some situations for medical treatment and provide timely information that previously has not been immediately available or available with confirmation of dispensed medication.

A further example of the integration of the system and test results is with respect to a critical medication that is stored and only available for dispensing in a predetermined manner. For example if the test results reveal a critical condition that was earlier considered as a possibility, a critical medication can be dispensed upon the predetermined conditions are met. This can provide a very fast response in a critical condition recognized by the onsite or in home unit. It is also possible to have a medication replaced with an alternate medication if certain predetermined conditions (programmed into the system and approved by the medical professional) are met. Thus alternate medications can be dispensed.

With this system high risk situations, can be programmed to allow almost immediate response with the critical medication dispensed by the system. Medication variations and/or medication alternates can also be programmed for fast convenience response. The above situations have been described relative to test results but other approaches included patient or user override are also possible. Such actions may require immediate reporting or an alert signal to a monitoring agency or medical professional.

Microchip technology and in particular microchip technology associated with medical assessment, treatment and diagnostic capabilities have increased extensively and now are used to confirm that certain medication has been taken on a daily basis and other routine functions, such as preliminary body testing or tracking. More sophisticated applications include providing a transmitter with a microchip that is swallowed or otherwise inserted into the body for providing detailed information with respect to a particular matter of interest. For example, microchips and local transmitters are now embedded in a capsule which is swallowed by a user to provide detailed assessment of the gastro track. Tracked information can include a number of sensors such as temperature pH and rate of travel information to provide assessment of the gastro track. This is helpful in diagnosing diseases such as Crone's disease or other diseases where the prior standard was to effectively use invasive procedures and samples of the gastro track. Such microchip technology can also provide image information that allows for assessment for the medical professional.

The detailed information is transmitted by the transmitter and is typically received by an associated transmitter worn or carried by the user. Thus the information can be over a particular period of time and will provide a host of particular test points.

Much like a heart monitoring system where the data is provided to a receiver, the receiver could be returned to a medical outlet or lab for processing an assessment. In the present application, the microchip technology for use in providing medications monitoring and/or medical testing procedures is advantageously used and the data can be tracked by a device worn or carried by the user. This device can then be connected to the medication processing unit and the information downloaded thereto. The communication capability of the device allows the information to be appropriately sent to medical authorities as well as initial processing may be carried out on site.

To assist in the recording of this information the particular microchip and transmitter that is provided to the user for initiating this test can also include information for entry into the medical tracking device. This information can include a database structure whereby the receiver can easily be connected to the device and the information is appropriately downloaded to the formed database.

Although this arrangement provides a simple approach for transmitting the collected data to the appropriate doctor or doctors it also provides a record of this information for the user. It can also be appreciated that this type of technology allows for a relatively convenient second test to confirm the results from an earlier test. The medication cassette system can also effectively conduct comparisons of the data assuming the tests are the same to determine points of differences and an assessment of the accuracy of the test.

At the present point in time the technology continues to evolve and as such the detailed information from a microchip based test is certainly of value initially but may be of assistance in future assessment. As the data is retained in its raw source and/or can be exported to an appropriate storage arrangement a user is provided with a simple method for allowing for a second opinion or a new assessment given that the technology may have changed over time.

It is believed that the microchip transmitter technology and the microchip monitoring systems as presently proposed are advantageously tracked with the present system to provide a more complete medical record for the user.

Variations of this system will be apparent to a person skilled in this art and are within the scope of the present invention.

The embodiments of the invention in which an exclusive property or privilege is claimed are defined as follows:

1. An automated system for medication dispensing and control comprising
    a computer processing arrangement;
    a medication receiving structure for receiving a series of medication cassettes assigned to at least one individual user with each medication cassette being for a specific individual user and an arrangement for dispensing of an alert response medication based on detection of a predetermined alert condition;
    an arrangement for receiving information associated with each medication cassette identifying the specific user, a quantity of medication and a dosage regime;
    a computer database associated with said computer processor arrangement for storing said received information;
    a medication dispensing arrangement associated with said medication receiving structure for dispensing of individual dosages of medication contained in said cassettes and tracking of said dispensed dosages by user in said computer database;
    a communication arrangement for connecting test equipment to said system and entering and storing user test results in said computer database;
    said computer processing arrangement including preliminary analysis of said dispensed medication and said test results of the specific user to identify the occurrence of said predetermined alert condition associated with the user;
    said computer processing arrangement upon identification of said predetermined alert condition dispenses or makes available for dispensing said alert response medication; and
    wherein said medication receiving structure is a rotary drum having a series of slots spread about a periphery thereof where each slot receives a medication cassette; and
    wherein said rotary drum rotates about a horizontal axis and receives cassettes at an upper position and dispenses medication when the cassette has been moved by rotating said drum to position the cassette adjacent a dispensing station at a lower edge of said rotary drum.

2. A system as claimed in claim 1 wherein said system includes a communication arrangement for sending of information to one or more predetermined addresses stored in said computer database.

3. A system as claimed in claim 2 wherein said communication arrangement automatically sends information specific to a detected predetermined alert condition associated with any user to a predetermined address entered in said database with respect to the specific user.

4. A system as claimed in claim 2 wherein said alert conditions include failure to dispense a medication according to the dispensing regime.

5. A system as claimed in claim 4 wherein said series of slots of said rotary drum is at least 8 slots spaced about a periphery thereof.

6. A system as claimed in claim 1 wherein said dispensing station includes a medication container for receiving medication of a user for daily use and a displacement actuating arrangement controlled by said computer processing arrangement to position said medication container beneath said dispensing station to receive medication into individual cells within said medication container.

7. A system as claimed in claim 1 wherein said system includes monitored predetermined conditions for executing a variation of a given medication dispensing regime.

8. A system as claimed in claim 7 wherein said variation of a given medication dispensing regime includes a change in dosage of a given medication or dispensing of an alternate medication.

9. A system as claimed in claim 7 wherein said predetermined conditions include monitored test results or a user input override or a combination of monitored test results and a user override.

* * * * *